(12) United States Patent
Huang

(10) Patent No.: US 9,206,407 B2
(45) Date of Patent: Dec. 8, 2015

(54) CHEMICALLY MODIFIED SOPHOROLIPIDS AND USES THEREOF

(75) Inventor: Tom Tao Huang, Fremont, CA (US)

(73) Assignee: Sophoro Biotechnologies, LLC, Sunnyvale, CA (US)

( * ) Notice: Subject to any disclaimer, the term of this patent is extended or adjusted under 35 U.S.C. 154(b) by 158 days.

(21) Appl. No.: 14/127,798

(22) PCT Filed: Jun. 25, 2012

(86) PCT No.: PCT/US2012/044072
§ 371 (c)(1),
(2), (4) Date: May 22, 2014

(87) PCT Pub. No.: WO2013/003291
PCT Pub. Date: Jan. 3, 2013

(65) Prior Publication Data
US 2014/0322755 A1   Oct. 30, 2014

Related U.S. Application Data

(60) Provisional application No. 61/501,179, filed on Jun. 25, 2011, provisional application No. 61/617,583, filed on Mar. 29, 2012.

(51) Int. Cl.
| | |
|---|---|
| *A61K 31/70* | (2006.01) |
| *C12N 9/42* | (2006.01) |
| *C07H 13/06* | (2006.01) |
| *C12P 21/00* | (2006.01) |
| *C12P 19/12* | (2006.01) |
| *C12P 7/64* | (2006.01) |

(52) U.S. Cl.
CPC .............. *C12N 9/2437* (2013.01); *C07H 13/06* (2013.01); *C12P 7/6436* (2013.01); *C12P 19/12* (2013.01); *C12P 21/00* (2013.01)

(58) Field of Classification Search
CPC ...... C07H 13/07; C12N 9/2437; C12P 21/00; C12P 19/12; C12P 7/6436
See application file for complete search history.

(56) References Cited

U.S. PATENT DOCUMENTS

| | | | |
|---|---|---|---|
| 4,818,816 | A | 4/1989 | Petitou |
| 5,981,497 | A | 11/1999 | Maingault |
| 6,433,152 | B1 | 8/2002 | Lang |
| 2006/0199244 | A1 | 9/2006 | Ashby |
| 2008/0076165 | A1 | 3/2008 | Gross |
| 2008/0241885 | A1 | 10/2008 | Ju |
| 2009/0008325 | A1 | 1/2009 | Ju |
| 2010/0009408 | A1 | 1/2010 | England |

OTHER PUBLICATIONS

International Search Report, PCT/US2012/044072, dated Jan. 30, 2013.
Written Opinion, PCT/US2012/044072, dated Jan. 30, 2013.
Asmer, et al., "Microbial production, structure elucidation and bioconversion of sophorose lipids", J. Am. Oil Chem. Society, 1988, 65(9):1460-1466.
Davila, et al., "Identification and determination of individual sophorolipids in fermentation products by gradient elution high-performance liquid chromatography with evaporative light-scattering detection", Journal of Chromatography, 1993, 648:139-149.
Davila et al., "Sophorose lipid production from lipidic precursors: predictive evaluation of industrial substrates", J. Indust. Microbiology, 1994, 13:249-257.
Esterbauer, H. et al., "Production of Trichoderma Cellulase in Laboratory and Pilot Scale", Bioresource Technology, 1991, 36:51-65.
Fleurackers, S.J.J., "On the Use of Waste Frying Oil in the Synthesis of Sophorolipids", Eur. J. Lipid Sci. Techol., 2006, 108:5-12.
Kubicek, C. P., et al., "Metabolic Engineering Strategies for the Improvement of Cellulase Production by Hypocrea jecorina," Biotechnology for Biofuels, 2009, 2:19.
Kurtzman et al., "Production of sophorolipid biosurfactants by multiple species of the Starmerella (Candida) bombicola yeast Glade", FEMS Microbiol. Lett., 2010, 311:140-146.
Mandels, M. et al., "Sophorose as an Inducer of Cellulase in Trichoderma viride," J. Bacteriol., 1962, 83(2):400-408.
Pen Fold, J. et al., "Solution Self-Assembly of the Sophorolipid Biosurfactant and Its Mixture with Anionic Surfactant Sodium Dodecyl Benzene Sulfonate", Langmuir, 2011, 27:8867-8877.
Ratsep, et al., "Identification and quantification of sophorolipid analogs using ultra-fast liquid chromatography-mass spectrometry", J. Microbiological Methods, 2009, 78:354-356.
Rau, U. et al., "Sophorolipids: a Source for Novel Compounds," Industrial Crops Products, 2001, 13:85-92.
Thompson, A. et al., "Acid Reversion Products from D-Glucose," J. Am. Chem. Soc., 1954, 76(5):1309-1311.
Van Bogaert, I. N. A., et al., "Microbial Synthesis of Sophorolipids," Process Biochemistry, 2011, 46(4):821-833.

*Primary Examiner* — Elli Peselev
(74) *Attorney, Agent, or Firm* — HelixIP LLP

(57) ABSTRACT

The present disclosure provides a sophorolipid composition that can be used for inducing protein expression in a fermentation host. The sophorolipid composition described herein can be prepared from a natural sophorolipid mixture. Acid treatment of the natural sophorolipid mixture results in a mixture of monoacetylated, deacetylated, and/or diacetylated sophorolipids. The chemically modified sophorolipid composition, or isolated components of the chemically modified sophorolipid composition, can be used as inducers for protein production in filamentous fungi.

11 Claims, 10 Drawing Sheets

A

B

A

B

C

D

A

B

C

D

E

F

G

H

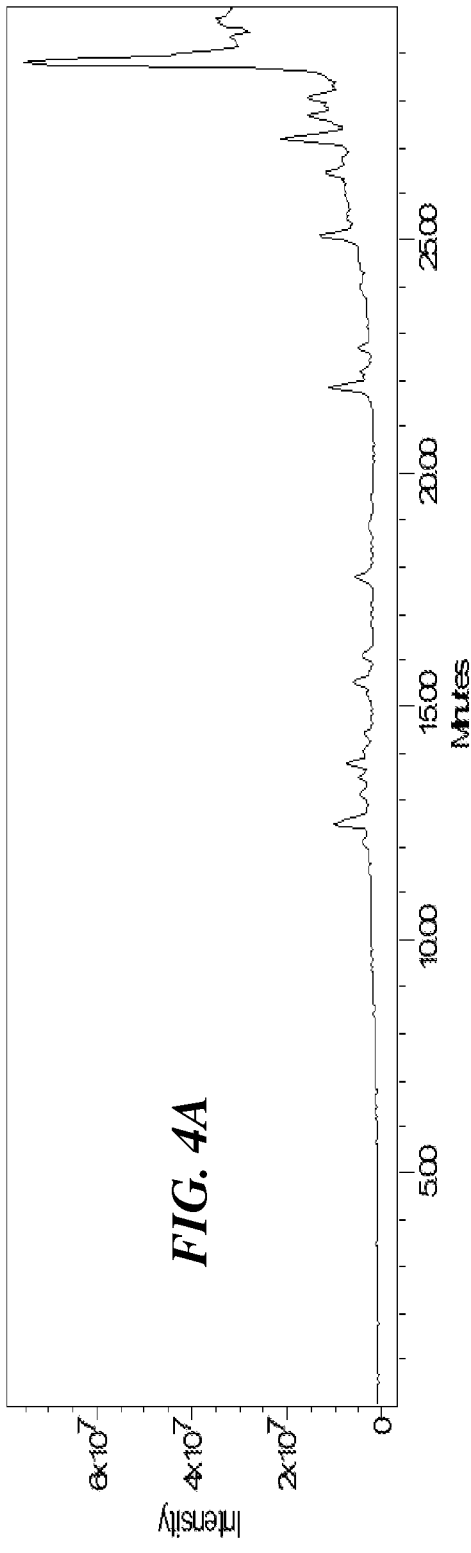
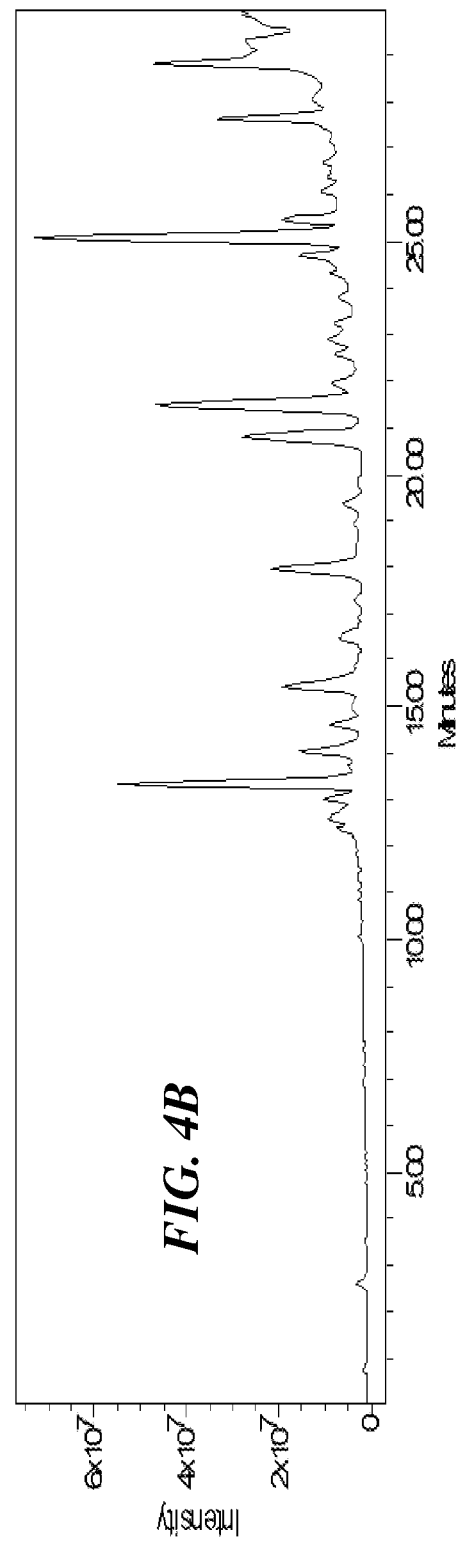
FIG. 4A
FIG. 4B

CHEMICALLY MODIFIED SOPHOROLIPIDS AND USES THEREOF

CROSS-REFERENCE TO RELATED APPLICATIONS

This application claims the benefit of U.S. Provisional Patent Application Ser. No. 61/501,179, filed Jun. 25, 2011, and U.S. Provisional Patent Application Ser. No. 61/617,583, filed Mar. 29, 2012, both of which are incorporated herein by reference in their entireties.

TECHNICAL FIELD

The present disclosure relates generally to sophorolipids that can be used as protein inducers, and more specifically to chemically modified sophorolipids that can be used as inducers for industrial cellulase production, as well as production of other proteins.

BACKGROUND OF THE INVENTION

Cellulose is an abundant, renewable biopolymer that can serve as building blocks for biofuels, bioplastics and other biochemicals. Enzymatic hydrolysis of cellulose to glucose by cellulase is the first step in converting this abundant biomass into bio-based products. Cellulase typically refers to a mixture of enzymes that includes (1) endoglucanases, which attack randomly within the cellulose fiber; (2) exoglucanases, which attack the end of fibers; and (3) beta-glucosidases, which hydrolyze small cellulose fragments to glucose.

Cellulases are typically produced on an industrial scale using *Trichoderma reesei*, a filamentous fungus that secretes high levels of cellulases when grown aerobically in the presence of cellulase inducers. Cellobiose and lactose are two effective inducers widely used in the industry for cellulase production in *Trichoderma reesei*. See Kubicek et al., *Biotechnology for Biofuels*, 2:19 (2009). Due to increasing costs of cellobiose and lactose, however, enzyme manufacturers have turned to alternative inducers.

Sophorose (2-O-beta-D-glucopyranosyl-alpha-D-glucose) has also been recognized as a good inducer for cellulase synthesis in *Trichoderma*. See Kubicek et al., *Biotechnology for Biofuels*, 2:19 (2009). Sophorose has been found to be a powerful inducer of a cellulase gene promoter sequence in *Trichoderma viride*, increasing cellulase production by about 2500 times compared to cellobiose. See Mandels et al., *J. Bacteriol.*, 83(2): 400-408 (1962). The costs associated with sophorose, however, have limited its use in industrial cellulase production.

First, sophorose is considered a "non-gratuitous" inducer because sophorose is metabolized by *Trichoderma* during fermentation. As a result, sophorose needs to be continually supplied during the fermentation process in order to achieve optimum induction. Second, sophorose is typically produced through glucose reversion reactions using either acids or enzymes. See e.g., England et al., U.S. Published Patent Application No. 2010/0009408; Thompson et al., *J. Am. Chem. Soc.*, 76(5):1309-1311, (1962). These reversion reactions often require reaction times ranging from hours to days. Further, these reversion reactions typically yield a mixture of products with a low concentration of sophorose in a high-concentration glucose background, where typical glucose to sophorose ratios range from 30:1 to 60:1. The sophorose is typically difficult to concentrate and purify cost-effectively from the product mixtures of these reversion reactions.

Other sophorose-containing molecules (also known as sophorosides) have been considered as potential inducers for industrial cellulase production. For example, sophorolipids naturally produced by the yeast *Candida bombicola* have been found to have protein inducing abilities. See Gross et al., U.S. 2008/0076165; Ju et al., U.S. 2008/0241885. The sophorolipids naturally secreted by *Candida bombicola* typically consist of one sophorose molecule (about 50% by weight) linked to a hydroxylated fatty acid. Two natural sophorolipids produced by *Candida bombicola* are depicted in FIG. 1. These natural sophorolipids are usually found as a mixture of lactonic sophorolipids and sophorolipids with fatty acid chains. The compound in FIG. 1A is a naturally produced lactonic sophorolipid containing acetyl groups at both the C6" and C6' positions. The compound in FIG. 1B is a naturally produced acidic sophorolipid containing acetyl groups at both the C6" and C6' positions. See also Gross et al., U.S. 2008/0076165; Van Bogaert et al., *Process Biochemistry*, 46(4): 821-833 (2011). Natural sophorolipids, however, have not been observed to have sufficient protein induction ability in *Trichoderma* to produce cellulases on an industrial scale.

Thus, there exists a need in the art for an inducer for cellulase production, as well as production of other proteins, that can be produced viably on commercial scale.

SUMMARY OF THE INVENTION

The present disclosure addresses this need by providing sophorolipid compounds suitable for inducing protein production. The sophorolipid compounds provided herein are chemically modified to increase protein activity by several folds compared to a natural sophorolipid mixture, sophorose, cellobiose and lactose. These chemically modified sophorolipid compounds can be prepared by acid hydrolysis of the natural sophorolipid mixture produced by, for example, the yeast *Candida bombicola*.

In one aspect, provided is a compound having the structure of formula (Ia) or (Ib):

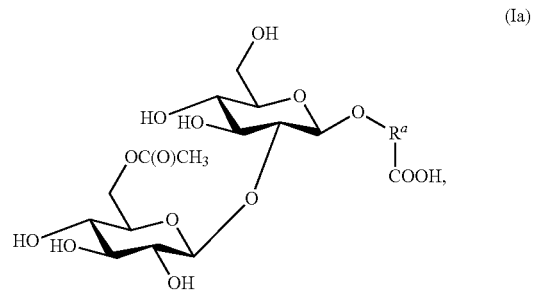

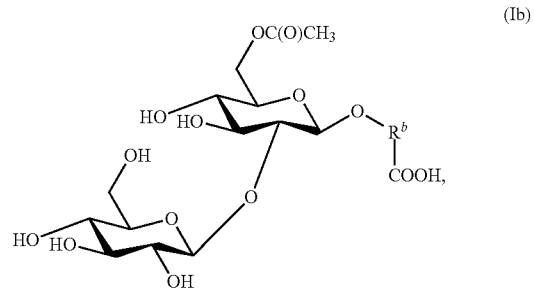

in which $R^a$ or $R^b$ is a C15-C18 alkylene or a C15-C18 alkenylene; and provided that when $R^a$ or $R^b$ is a C18 alkenylene, the C18 alkenylene is polyunsaturated.

In some embodiments, each $R^a$ and $R^b$ is independently an unsubstituted C15-C18 alkyl or an unsubstituted C15-C18 alkenylene. In other embodiments, $R^a$ or $R^b$ is each independently selected from an unsubstituted, unbranched C15-C18 alkylene; an unsubstituted, branched C15-C18 alkylene; an unsubstituted, unbranched C15-C18 alkenylene; and an unsubstituted, branched C15-C18 alkenylene. In yet other embodiments, each $R^a$ and $R^b$ is independently selected from C15 alkylene, C16 alkenylene, C17 alkylene and C18 alkenylene.

In one embodiment, the compound is selected from:

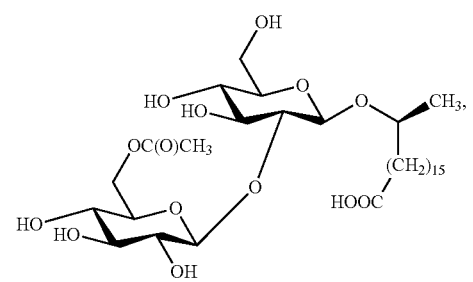

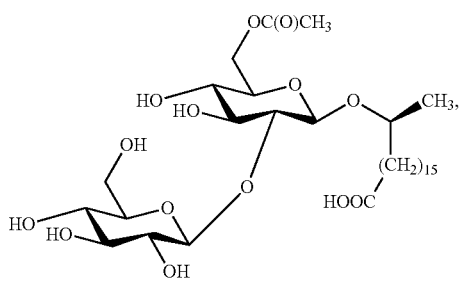

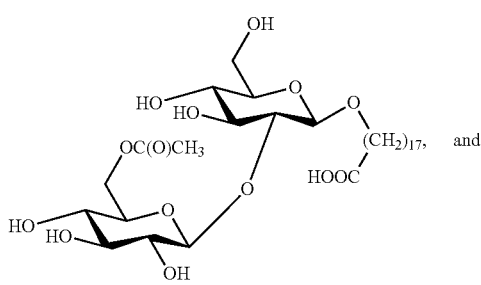

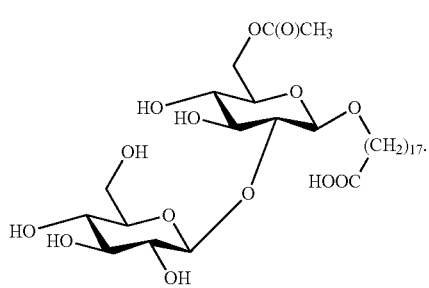

In another aspect, provided is a compound having a structure of formula (II):

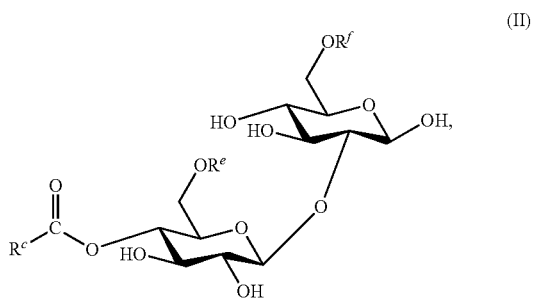

in which:
$R^c$ is an aliphatic moiety;
$R^e$ is H or $C(O)CH_3$; and
$R^f$ is H or $C(O)CH_3$.

In some embodiments, $R^c$ is an aliphatic moiety selected from unsubstituted C1-C24 alkyl, substituted C1-C24 alkyl, unsubstituted C2-C24 alkenyl, substituted C2-C24 alkenyl, unsubstituted C2-C24 alkynyl, and substituted C2-C24 alkynyl. In certain embodiments, $R^c$ is an aliphatic moiety selected from unsubstituted C1-C24 alkyl, C1-C24 alkyl substituted with hydroxyl, unsubstituted C2-C24 alkenyl, C2-C24 alkenyl substituted with hydroxyl, unsubstituted C2-C24 alkynyl, and C2-C24 alkynyl substituted with hydroxyl. When $R^c$ is alkyl, alkenyl, or alkynyl substituted with hydroxyl, the compound of formula (II) has a fatty alcohol chain.

In certain embodiments, $R^c$ is an aliphatic moiety selected from unsubstituted C5-C24 alkyl, substituted C5-C24 alkyl, unsubstituted C5-C24 alkenyl, substituted C5-C24 alkenyl, unsubstituted C5-C24 alkynyl, and substituted C5-C24 alkynyl. In certain embodiments, $R^c$ is an aliphatic moiety selected from unsubstituted C5-C24 alkyl, C5-C24 alkyl substituted with hydroxyl, unsubstituted C5-C24 alkenyl, C5-C24 alkenyl substituted with hydroxyl, unsubstituted C5-C24 alkynyl, and C5-C24 alkynyl substituted with hydroxyl.

In certain embodiments, $R^c$ is an aliphatic moiety selected from unsubstituted C15-C18 alkyl, substituted C15-C18 alkyl, unsubstituted C15-C18 alkenyl, substituted C15-C18 alkenyl, unsubstituted C15-C18 alkynyl, and substituted C15-C18 alkynyl. In certain embodiments, the aliphatic moiety of $R^c$ is selected from the group consisting of unsubstituted C15-C18 alkyl, C15-C18 alkyl substituted with hydroxyl, unsubstituted C15-C18 alkenyl, C15-C18 alkenyl substituted with hydroxyl, unsubstituted C15-C18 alkynyl, and C15-C18 alkynyl substituted with hydroxyl.

In certain embodiments, $R^c$ is an aliphatic moiety selected from unsubstituted C15 alkyl, substituted C15 alkyl, unsubstituted C17 alkyl, substituted C17 alkyl, unsubstituted C16 alkenyl, substituted C16 alkenyl, unsubstituted C18 alkenyl, and substituted C18 alkenyl. In certain embodiments, $R^c$ is an aliphatic moiety selected from unsubstituted C15 alkyl, C15 alkyl substituted with hydroxyl, unsubstituted C17 alkyl, C17 alkyl substituted with hydroxyl, unsubstituted C16 alkenyl, C16 alkenyl substituted with hydroxyl, unsubstituted C18 alkenyl, and C18 alkenyl substituted with hydroxyl.

In certain embodiments, $R^c$ is an aliphatic moiety selected from C15-C18 alkyl substituted with hydroxyl, and C15-C18 alkenyl substituted with hydroxyl.

In some embodiments, $R^e$ is H. In other embodiments, $R^e$ is $C(O)CH_3$. In some embodiments, $R^f$ is H. In other embodiments, $R^f$ is C(O)CH$_3$. In certain embodiments, $R^e$ is H or C(O)CH$_3$, and $R^f$ is H. In other embodiments, $R^e$ is H, and $R^f$ is H or C(O)CH$_3$.

In some embodiments, the compound of formula (II) has a structure of formula (IIa), (IIb), (IIc) or (IId):

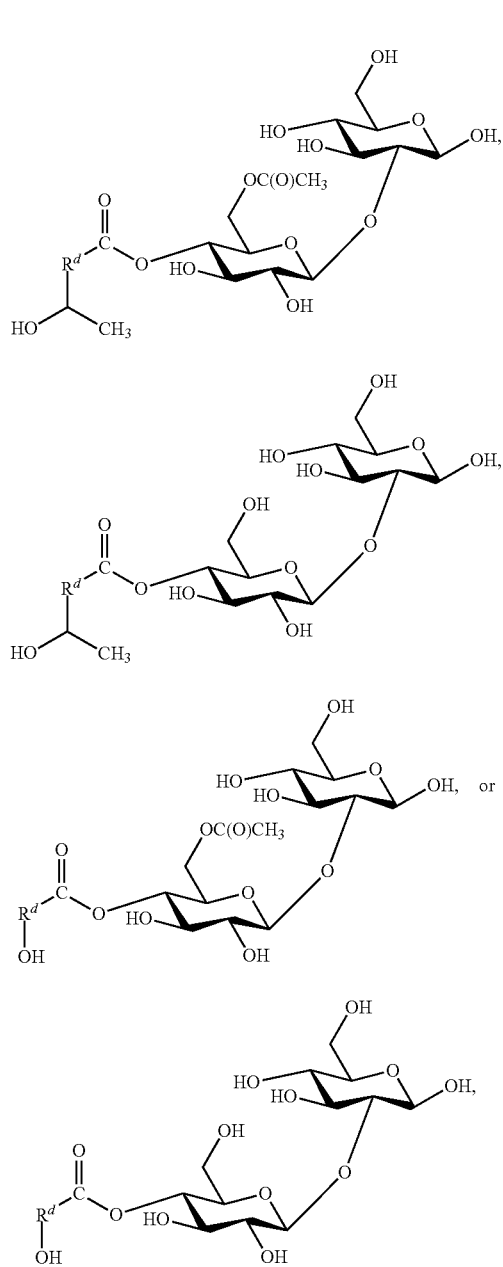

in which $R^d$ is an aliphatic moiety.

In some embodiments, $R^d$ is an aliphatic moiety selected from unsubstituted C1-C24 alkylene, unsubstituted C2-C24 alkenylene, and unsubstituted C3-C24 alkynylene. In certain embodiments, $R^d$ is an aliphatic moiety selected from unsubstituted C5-C24 alkylene, unsubstituted C5-C24 alkenylene, and unsubstituted C5-C24 alkynylene. In certain embodiments, $R^d$ is an aliphatic moiety selected from unsubstituted C15-C18 alkylene, unsubstituted C15-C18 alkenylene, and unsubstituted C15-C18 alkynylene.

In one embodiment, the compound of formula (II) is selected from:

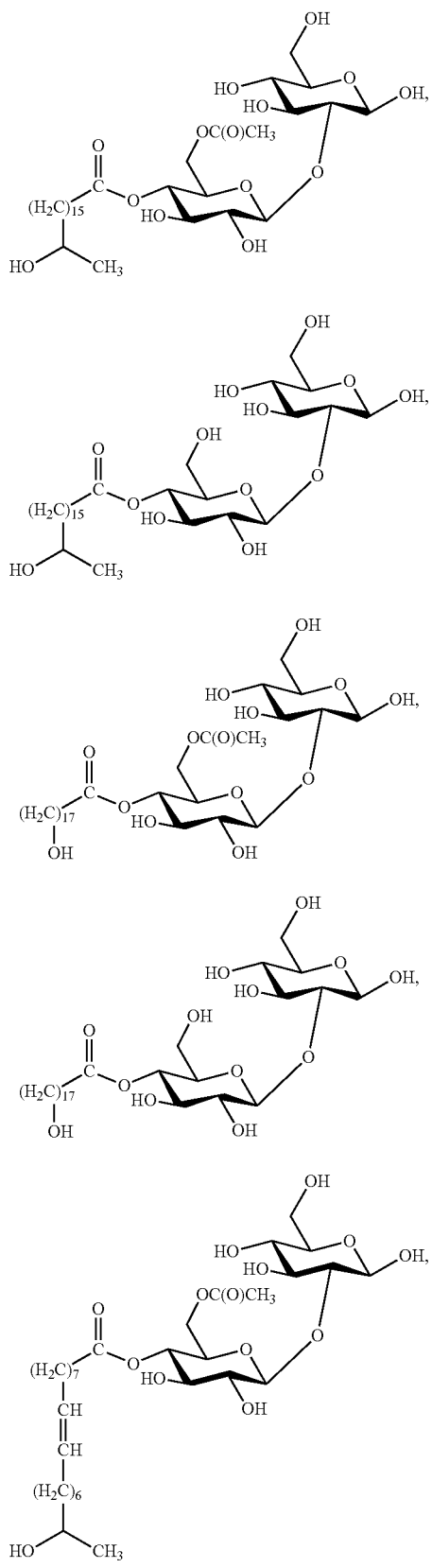

-continued

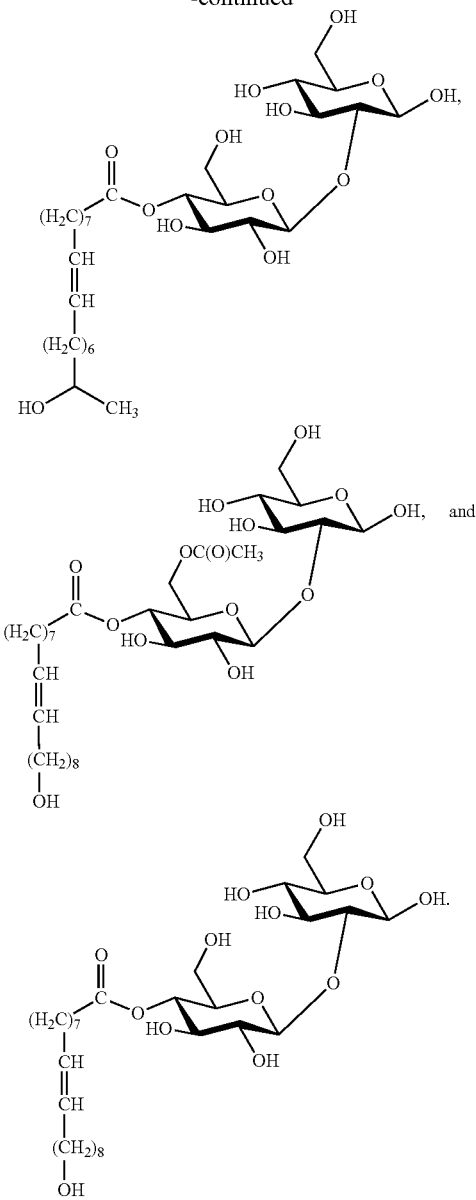

In some embodiments, the compound of formula (II), (IIa), (IIb), (IIc) or (IId) has an inductive effect for protein production in a fermentation host of at least two times, at least three times, at least four times, at least five times, at least a ten-fold, at least a twenty-fold, at least a thirty-fold, at least a forty-fold, at least a fifty-fold, at least a hundred-fold, at least a two hundred-fold, or at least a two hundred fifty-fold times greater than a natural sophorolipid mixture produced. In certain embodiments, the protein may be an enzyme, a hormone, a growth factor, a cytokine, a vaccine, an antibody, or a polypeptide. In certain embodiments, the protein is an enzyme. In one embodiment, the protein is cellulase. In some embodiments, the natural sophorolipid mixture is produced by a *Candida* host. In one embodiment, the natural sophorolipid mixture is produced by *Candida bombicola* or *Candida apicola*.

In some embodiments, the compound of formula (II), (IIa), (IIb), (IIc) or (IId) has an inductive effect for protein production in a fermentation host of at least five times, at least six times, at least seven times, at least eight times, at least nine times, at least ten times, at least fifty times, or at least a hundred times greater than sophorose.

Provided is also a composition that includes one or more monoacetylated acidic sophorolipids; and one or more compounds selected from a deacetylated acidic sophorolipid, a deacetylated glucolipid, a diacetylated acidic sophorolipid, a deacetylated lactonic sophorolipid, a monoacetylated lactonic sophorolipid, and a diacetylated lactonic sophorolipid, in which the one or more monoacetylated acidic sophorolipids is at least 5% by weight of the composition. In other embodiments, the one or more monoacetylated acidic sophorolipids is at least 10%, at least 15%, at least 20%, at least 25%, at least 30%, at least 40%, at least 50%, at least 60%, at least 70%, at least 80%, at least 85%, at least 90%, at least 95% by weight of the composition. In certain embodiments of the composition, the one or more monoacetylated acidic sophorolipids has a formula (Ia) or (Ib).

In some embodiments, the composition has less than 50%, less than 40%, less than 30%, less than 20%, less than 10%, or less than 5% of one or more compounds selected from a deacetylated acidic sophorolipid, a deacetylated glucolipid, a diacetylated acidic sophorolipid, a deacetylated lactonic sophorolipid, a monoacetylated lactonic sophorolipid, and a diacetylated lactonic sophorolipid. In certain embodiments, the composition has less than 5% by weight of deacetylated acidic sophorolipids. In other embodiments, the composition has less than 15%, less than 10%, or less than 5% by weight of deacetylated lactonic sophorolipids. In yet other embodiments, the composition has less than 50%, less than 40%, less than 30%, less than 20%, less than 10%, or less than 5% by weight of monoacetylated lactonic sophorolipids. In yet other embodiments, the composition has less than 20%, less than 15%, less than 10%, or less than 5% by weight of diacetylated lactonic sophorolipids. In some embodiments, each of the one or more monoacetylated acidic sophorolipids independently has a structure of formula (Ia) or (Ib).

Provided is also a composition that includes one or more monoacetylated acidic sophorolipids, and one or more sophorolipid esters. In one embodiment, the composition includes one or more monoacetylated acidic sophorolipids of formula (Ia) or (Ib), and one or more sophorolipid esters of formula (II), (IIa), (IIb), (IIc), or (IId).

Provided is also a composition that includes one or more compounds of formula (II), (IIa), (IIb), (IIc), or (IId); and one or more compounds selected from the group consisting of a monoacetylated acidic sophorolipid, a diacetylated acidic sophorolipid, a deacetylated acidic sophorolipid, a monoacetylated lactonic sophorolipid, a diacetylated lactonic sophorolipid, a deacetylated lactonic sophorolipid, a monoacetylated glucolipid, a diacetylated glucolipid, and deacetylated glucolipid. In some embodiments, the one or more compounds of formula (II), (IIa), (IIb), (IIc), or (IId) is less than 0.5% by weight of the composition. In other embodiments, the one or more compounds of formula (II), (IIa), (IIb), (IIc), or (IId) is at least 0.5%, at least 1%, at least 5%, at least 10%, at least 20%, at least 30%, at least 40%, at least 50%, at least 60%, at least 70%, at least 80%, at least 90%, at least 95%, at least 99% by weight of the composition.

Provided is also a method for producing a protein of interest by: a) providing a fermentation host; and b) culturing the fermentation host with a carbon source and one or more compounds of formula (II), (IIa), (IIb), (IIc), or (IId), wherein the fermentation host is cultured under conditions sufficient to produce a protein of interest. In certain embodiments, the compounds of formula (II), (IIa), (IIb), (IIc), or (IId) used in the method described herein may be isolated after an acid treatment of a natural sophorolipid mixture. In other embodiments, a composition produced from acid treatment of a natural sophorolipid mixture that includes the compounds of formula (II), (IIa), (IIb), (IIc), or (IId) may be used in the method described herein.

In one embodiment, the protein of interest is cellulase. In some embodiments, the fermentation host is capable of producing cellulase. In some embodiments, the fermentation host is a filamentous fungus. Examples of suitable filamentous fungus may include *Trichoderma, Humicola, Pleurotus, Fusarium, Aspergillus, Streptomyces, Thermomonospora, Bacillus, Cellulomonas, Penicillium, Basidiomycete, Chrysoporium, Pestalotiopsis, Neurospora, Cephalosporium, Achlya, Podospora, Endothia, Mucor, Cochliobolus,* and *Pyricularia*. In one embodiment, the fermentation host is *Trichoderma reesei*. In other embodiments, the fermentation host has a promoter operably linked to a gene encoding a protein of interest. In some embodiments, the composition induces activity of the promoter. In certain embodiments, the promoter is a cellulase gene promoter. In one embodiment, the promoter is a cbh1 promoter. In other embodiments, the protein of interest is a homologous or heterologous protein. In certain embodiments, the homologous or heterologous protein may be an enzyme, a hormone, a growth factor, a cytokine or an antibody. In some embodiments, the carbon source is biomass. In certain embodiments, the biomass may include fatty acids, fatty esters, or fatty alcohols.

Provided is also a method for producing a composition that includes one or more compounds of formula (Ia), (Ib), (II), (IIa), (IIb), (IIc), or (IId), by: a) providing a natural sophorolipid mixture by fermentation of a biomass using *Candida bombicola* in a fermentation media; and b) contacting the natural sophorolipid mixture with an acid solution to produce the composition. In some embodiments, the contacting of the natural sophorolipid mixture with the acid solution further includes heating the natural sophorolipid mixture and the acid solution. In certain embodiments, the natural sophorolipid mixture and the acid solution are heated at a temperature of at least 50° C. In yet other embodiments, the method for producing a composition that includes one or more compounds of formula (Ia), (Ib), (II), (IIa), (IIb), (IIc), or (IId), further includes flocculating the chemically modified sophorolipid mixture; and isolating the flocs from the composition.

In some embodiments, the acid solution may include hydrochloric acid, sulfuric acid or nitric acid, or a mixture thereof.

In some embodiments, the biomass has fatty acids, fatty esters, fatty alcohols, or any combinations thereof. In certain embodiments, the biomass may have unsaturated or saturated fatty acids, such as for example palmitoleic acid, oleic acid, linoleic acid, palmitic acid, and stearic acid.

Provided is also a method for producing one or more compounds of formula (Ia), (Ib) (II), (IIa), (IIb), (IIc), or (IId), by: a) providing a natural sophorolipid mixture by fermentation of a biomass using *Candida bombicola* in a fermentation media; b) contacting the natural sophorolipid mixture with an acid solution to produce a composition having one or more compounds of formula (Ia), (Ib) (II), (IIa), (IIb), (IIc), or (IId); and c) isolating the one or more compounds from the composition.

Provided herein are also kits that include one or more compounds of formula (Ia), (Ib) (II), (IIa), (IIb), (IIc), or (IId); and instructions for use in the methods of producing a protein as described herein.

DETAILED DESCRIPTION

The following description sets forth exemplary methods, parameters and the like. It should be recognized, however, that such description is not intended as a limitation on the scope of the present disclosure but is instead provided as a description of exemplary embodiments.

Provided are chemically modified sophorolipids that can induce protein production. Provided are also methods of producing these sophorolipids by chemically modifying a natural sophorolipid mixture. In certain embodiments, these chemically modified sophorolipids can be isolated as solids. In other embodiments, these chemically modified sophorolipids can be further purified. Further, provided are methods of producing proteins, such as cellulase, using these chemically modified sophorolipids as inducing agents.

Chemically Modified Sophorolipids

The chemically modified sophorolipids and the natural sophorolipids from which these chemically modified sophorolipids are produced use the following atom numbering convention:

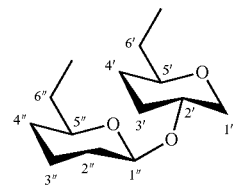

In one aspect, provided is a chemically modified sophorolipid composition that is produced by acid hydrolysis of a natural sophorolipid mixture. The composition may include a mixture of monoacetylated, deacetylated and diacetylated sophorolipids.

In certain embodiments, the composition includes at least one monoacetylated acidic sophorolipid. An acidic sophorolipid refers to a sophorolipid having an aliphatic moiety substituted with a carboxyl group.

Figure 2:
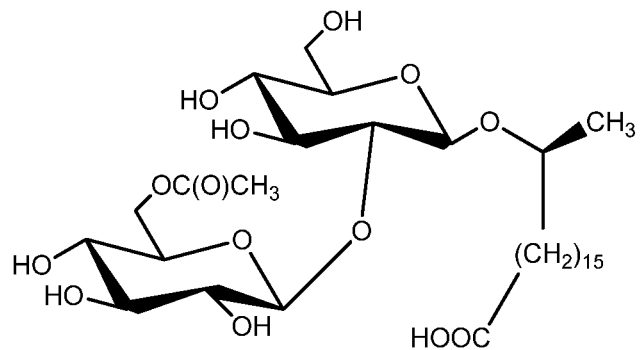
FIG. 2 depicts the chemical structures of four exemplary monoacetylated acidic sophorolipids produced by acid hydrolysis of a natural sophorolipid mixture.
Figure 2:
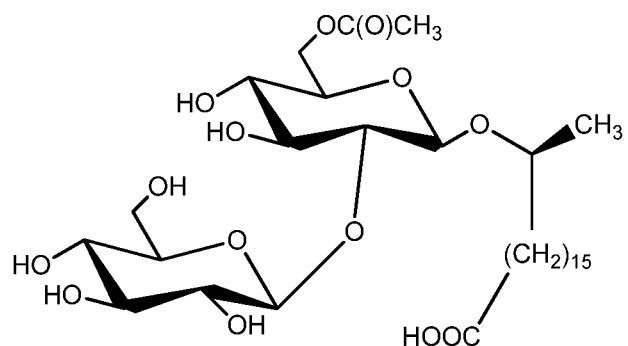
Figure 2:
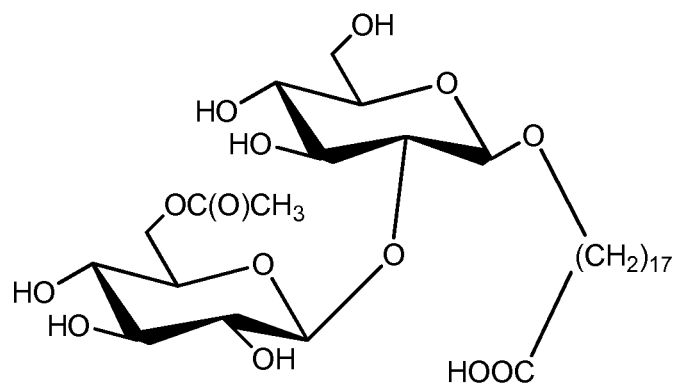
Figure 2:
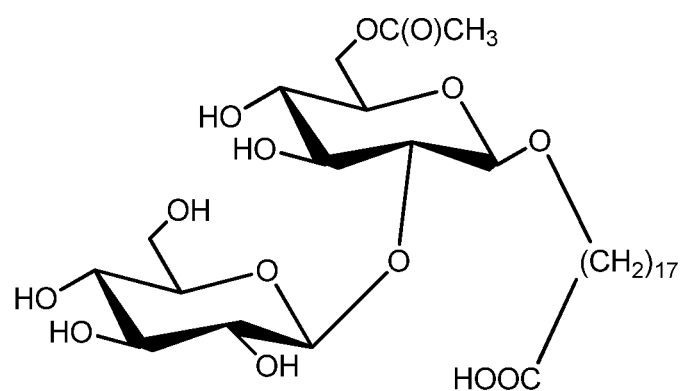

FIG. 2 depicts four exemplary monoacetylated acidic sophorolipids that may be produced by chemically modifying a natural sophorolipid mixture. These exemplary monoacetylated acidic sophorolipids in FIG. 2 are acetylated at either the C6" or C6' position, with a C18 fatty acid chain.

In other embodiments, the chemically modified sophorolipid composition includes at least one sophorolipid ester, in which the sophorolipid ester is a monoacetylated sophorolipid ester, a deacetylated sophorolipid ester, or a combination thereof. A sophorolipid ester refers to a non-cyclic sophorolipid molecule, with an aliphatic moiety attached to the sophorose molecule by an ester group.

In some embodiments, the sophorolipid ester is a compound having a structure of formula (II):

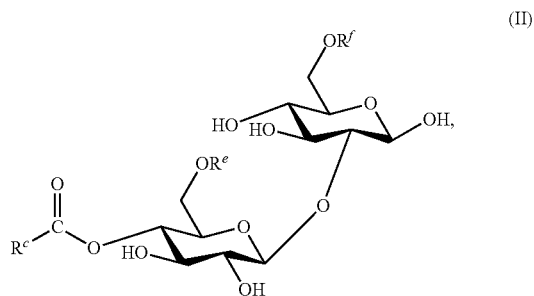
(II)

in which:

$R^c$ is an aliphatic moiety;

$R^e$ is H or $C(O)CH_3$; and $R^f$ is H or $C(O)CH_3$.

In other embodiments, the compound of formula (II) has a structure of formula (IIa), (IIb), (IIc) or (IId):

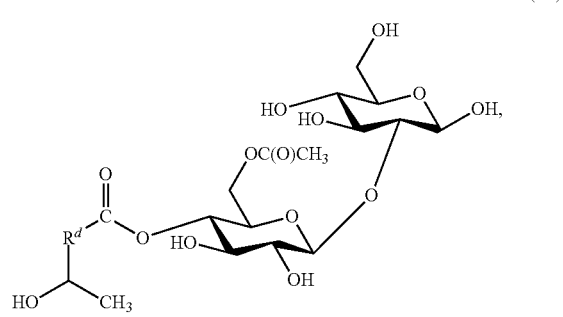
(IIa)

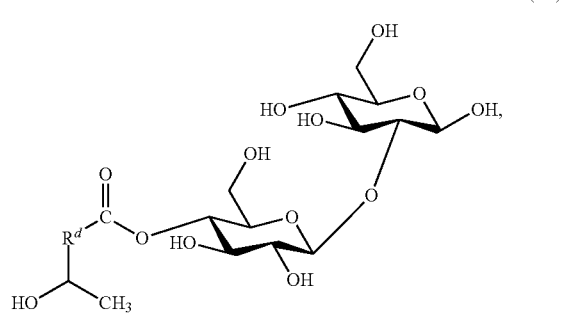
(IIb)

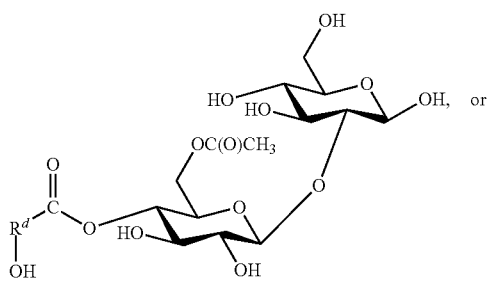
(IIc)

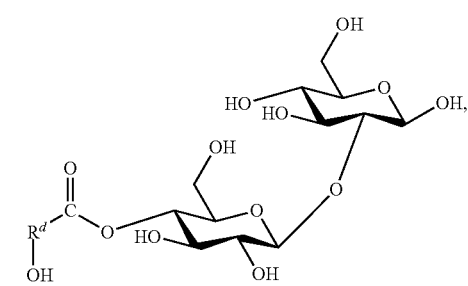
(IId)

in which $R^d$ is an aliphatic moiety.

As used herein, an "aliphatic" moiety is a non-aromatic carbon moiety. In some embodiments, an aliphatic moiety may include a linear, branched or cyclic carbon moiety. In certain embodiments, an aliphatic moiety may include a saturated or unsaturated moiety, including both monovalent and bivalent moieties. In some embodiments, the aliphatic moiety is an aliphatic alkyl, an aliphatic alkenyl, an aliphatic alkynyl, an aliphatic cycloalkyl, an aliphatic cycloalkenyl, an aliphatic cycloalkynyl, or any bivalent radicals thereof.

"Alkyl" includes saturated linear or branched hydrocarbon structures, and combinations of these, which contain only carbon and hydrogen atoms when unsubstituted. In some embodiments, alkyl groups have one to twenty-four carbon atoms (i.e., C1-C24 alkyl), five to twenty-four carbon atoms (i.e., C5-C24 alkyl), or fifteen to eighteen carbon atoms (i.e., C15-C18 alkyl). When an alkyl residue having a specific number of carbon atoms is named, all geometric isomers having that number of carbon atoms may be encompassed. For example, "butyl" may, in some embodiments, include n-butyl, sec-butyl, iso-butyl, and tert-butyl; "propyl" may, in some embodiments, include n-propyl and iso-propyl. In some embodiments, the alkyl group may be substituted. In one embodiment, substituted alkyl groups may have a hydroxyl substituent. Alkyl groups substituted with hydroxyl may include, for example, —$(CH_2)_{17}OH$ and —$(CH_2)_{15}CH(CH_3)$OH. In another embodiment, substituted alkyl groups may have a carboxyl substituent. Alkyl groups substituted with carboxyl may include, for example, —$(CH_2)_{17}COOH$.

"Cycloalkyl" refers to a cyclic alkyl group, and can have one ring (e.g., cyclohexyl) or multiple rings (e.g., adamantyl).

"Alkylene" refers to the same residues as alkyl, but having bivalency. Examples of alkylene include methylene (—$CH_2$—), ethylene (—$CH_2CH_2$—), propylene (—$CH_2CH_2CH_2$—), butylene (—$CH_2CH_2CH_2CH_2$—), as well as longer chains including —$(CH_2)_{17}$— and —$(CH_2)_{15}CH(CH_2)$—.

"Alkenyl" refers to an unsaturated hydrocarbon group having at least one site of olefinic unsaturation (i.e., having at least one moiety of the formula C=C). When the alkenyl has one site of olefinic unsaturation, the alkenyl is monounsaturated. When the alkenyl has two or more sites of olefinic unsaturation, the alkenyl is polyunsaturated. In some embodiments, alkenyl groups have two to twenty-four carbon atoms (i.e., C2-C24 alkenyl), five to twenty-four carbon atoms (i.e., C5-C24 alkenyl), or fifteen to eighteen carbon atoms (i.e., C15-C18 alkenyl). Alkenyl groups may include, for example, —CH$_2$—CH═CH—CH$_3$ and —(CH$_2$)$_7$—CH═CH—(CH$_2$)$_7$—CH—. In some embodiments, the alkenyl group may be substituted. In one embodiment, substituted alkenyl groups may have a hydroxyl substituent. Alkenyl groups substituted with hydroxyl may include, for example, —(CH$_2$)$_7$—CH═CH—(CH$_2$)$_8$—OH and —(CH$_2$)$_7$—CH═CH—(CH$_2$)$_6$—CH(CH$_3$)OH. In another embodiment, substituted alkenyl groups may have a carboxyl substituent. Alkenyl groups substituted with carboxyl may include, for example, —(CH$_2$)$_7$—CH═CH—(CH$_2$)$_8$—COOH.

"Cycloalkenyl" refers to a cyclic alkenyl group and can have one ring (e.g., cyclohexenyl, —CH$_2$—CH$_2$-cyclohexenyl), or multiple rings (e.g., norbornenyl).

"Alkenylene refers to the same residues as alkenyl, but having bivalency. Examples of alkenylene include ethylene (—CH═CH—), propylene (—CH$_2$—CH═CH—), butylene (—CH$_2$—CH═CH—CH$_2$—), as well as longer chains including —(CH$_2$)$_7$—CH═CH—(CH$_2$)$_8$— and —(CH$_2$)$_7$—CH═CH—(CH$_2$)$_6$—CH(CH$_2$)—.

"Alkynyl" refers to an unsaturated hydrocarbon group having at least one site of acetylenic unsaturation (i.e., having at least one moiety of the formula C≡C). When the alkynyl has one site of acetylenic unsaturation, the alkynyl is monounsaturated. When the alkynyl has two or more sites of acetylenic unsaturation, the alkynyl is polyunsaturated. In some embodiments, alkynyl groups have two to twenty-four carbon atoms (i.e., C2-C24 alkynyl), five to twenty-four carbon atoms (i.e., C5-C24 alkynyl), or fifteen to eighteen carbon atoms (i.e., C15-C18 alkynyl). Alkynyl groups may include, for example, —CH$_2$—C≡C—CH$_3$ and —(CH$_2$)$_7$—C≡C—(CH$_2$)$_7$—CH. In some embodiments, the alkynyl group may be substituted. In one embodiment, substituted alkynyl groups may have a hydroxyl substituent. Alkynyl groups substituted with hydroxyl may include, for example, —(CH$_2$)$_7$—C≡C—(CH$_2$)$_8$—OH and —(CH$_2$)$_7$—C—(CH$_2$)$_6$—CH(CH$_3$)OH. In another embodiment, substituted alkynyl groups may have a carboxyl substituent. Alkynyl groups substituted with carboxyl may include, for example, —(CH$_2$)$_7$—C≡C—(CH$_2$)$_8$—COOH.

"Cycloalkynyl" refers to a cyclic alkynyl group and can have one ring (e.g., cyclohexynyl), or multiple rings.

"Alkynylene" refers to the same residues as alkynyl, but having bivalency. Examples of alkynylene include butynylene (—C≡C—CH$_2$CH$_2$— and —CH$_2$—C≡C—CH$_2$—), as well as longer chains including —(CH$_2$)$_7$—C≡C—(CH$_2$)$_8$— and —(CH$_2$)$_7$—C≡C—(CH$_2$)$_6$—CH(CH$_2$)—.

Figure 3:
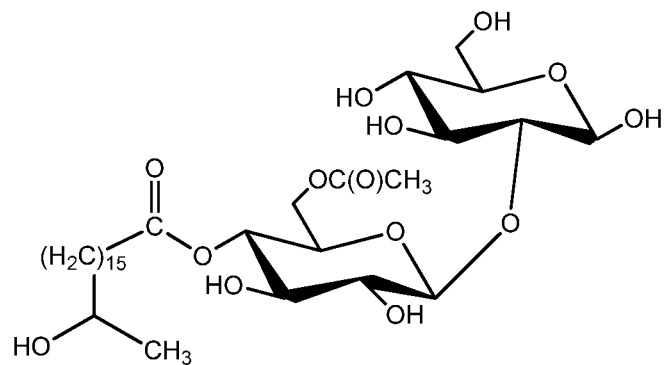
FIG. 3 depicts the chemical structures of eight exemplary sophorolipid esters produced by acid hydrolysis of a natural sophorolipid mixture.
Figure 3:
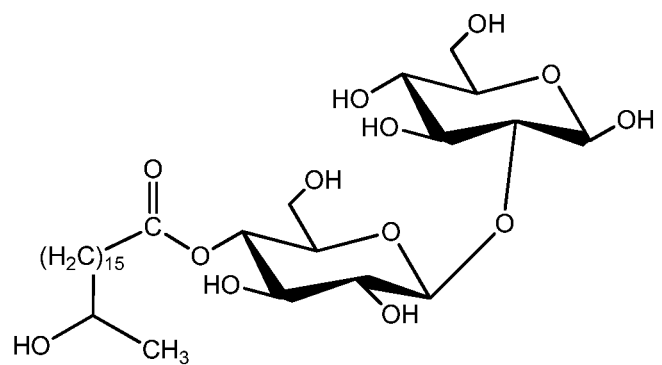
Figure 3:
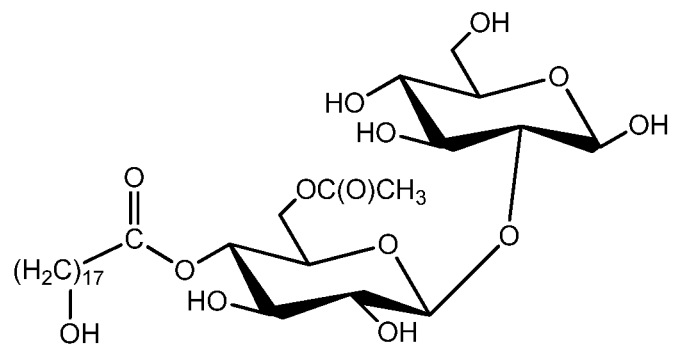
Figure 3:
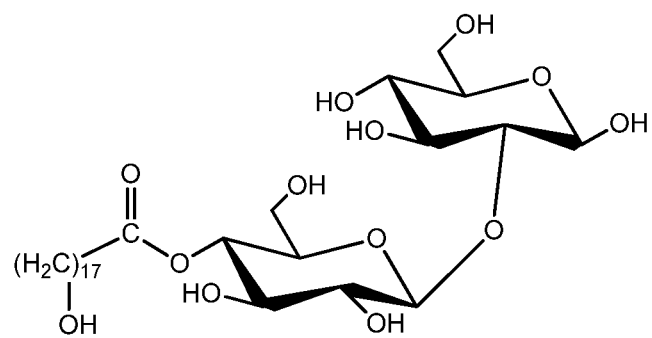
Figure 3:
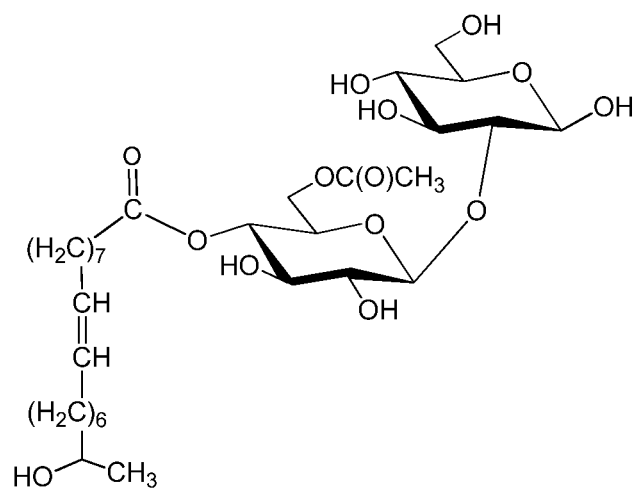
Figure 3:
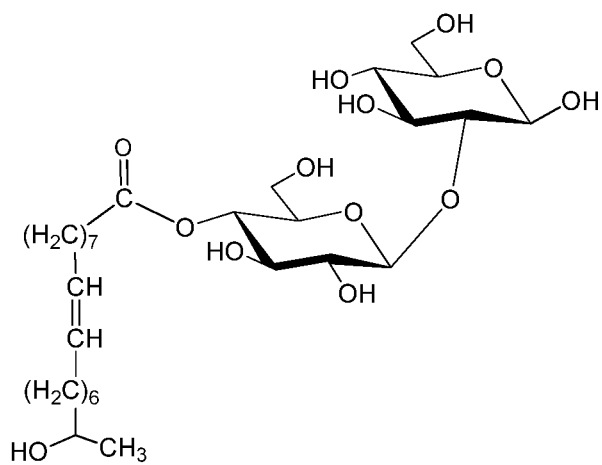
Figure 3:
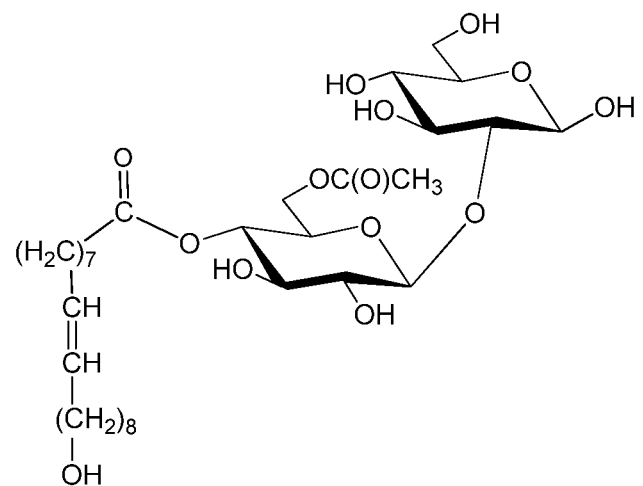
Figure 3:
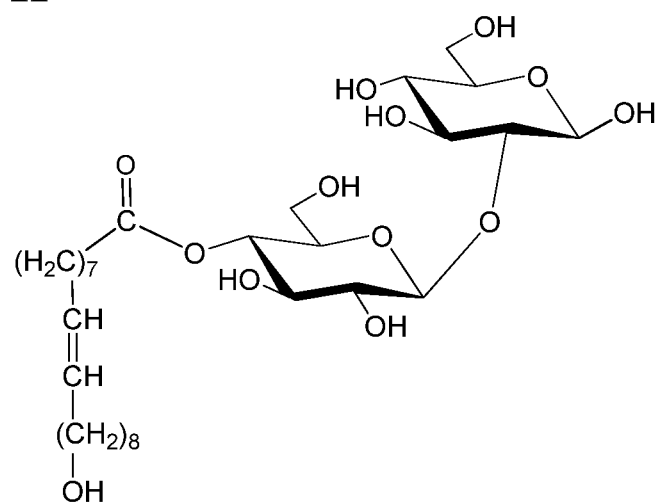
Figure 4C:
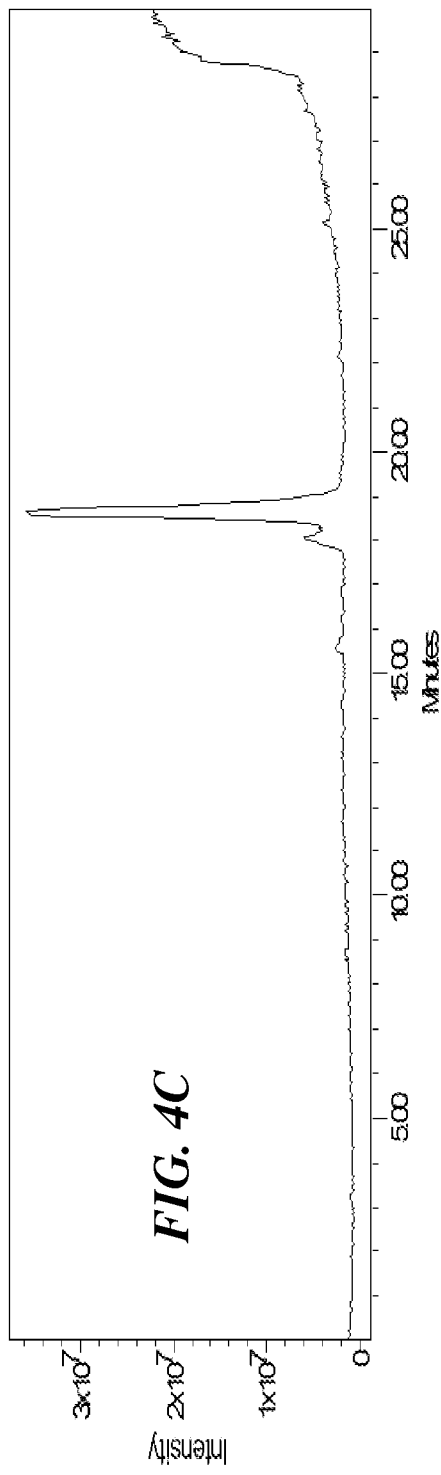
FIG. 4 shows the LC-MS total ion current (TIC) scans of: (A) the natural sophorolipid mixture; (B) the acid-treated sophorolipid mixture; (C) fraction 1 isolated from the acid-treated sophorolipid mixture; (D) fraction 2 isolated from the acid-treated sophorolipid mixture; and mass spectra of: (E) fraction 1; and (F) fraction 2.
Figure 4D:
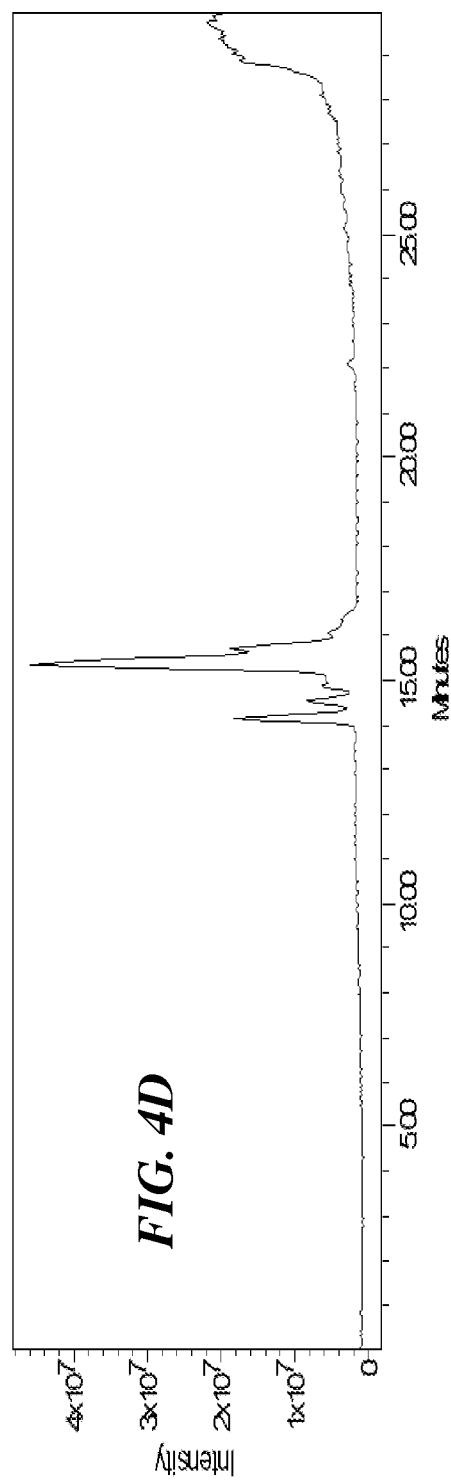
Figure 4E:
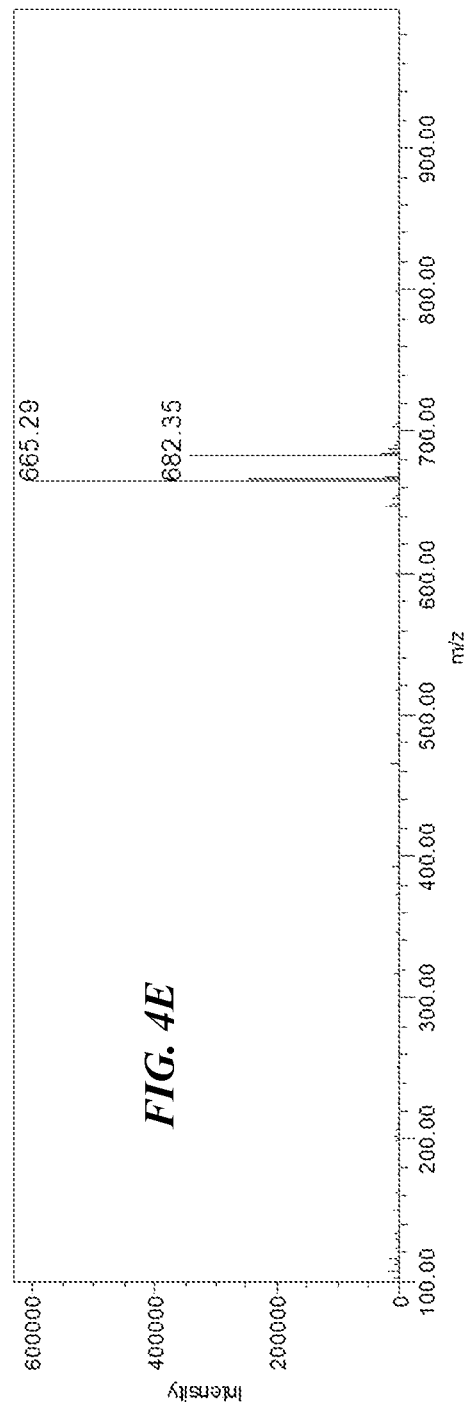
Figure 4F:
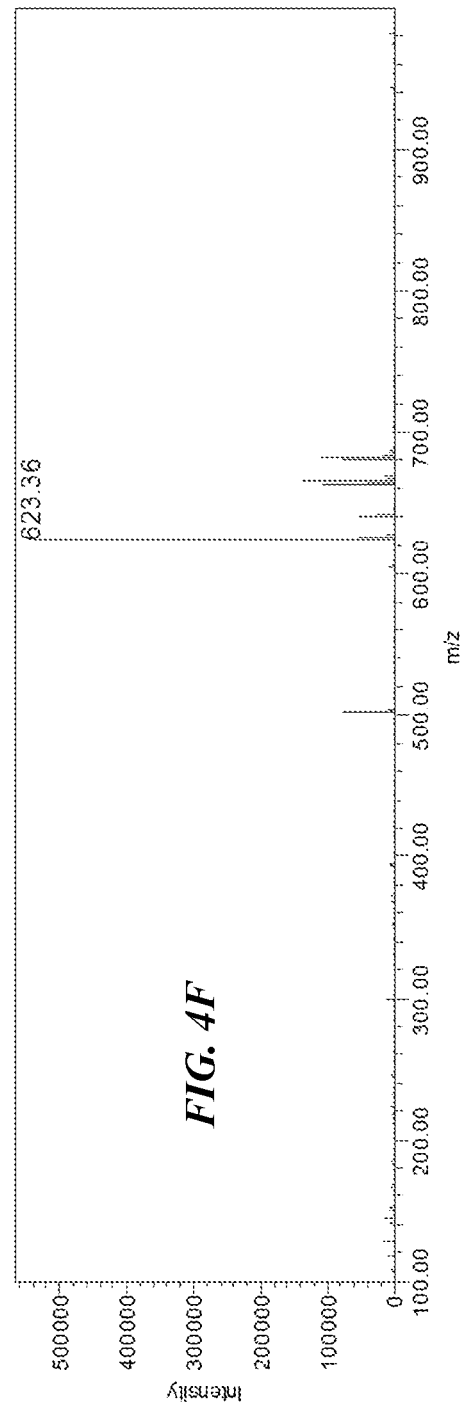

FIG. 3 depicts eight exemplary sophorolipid esters that may be produced by chemically modifying a natural sophorolipid mixture. These exemplary sophorolipid esters in FIG. 3 are esterified at the C4" position, and have a C18 fatty alcohol chain. In the exemplary embodiments, the fatty alcohol chain may be saturated or monounsaturated.

It should be understood, however, that the saturation and the length of the aliphatic moiety of the chemically modified sophorolipids described herein may vary depending on the type of biomass used for producing the natural sophorolipid mixture. In some embodiments, the aliphatic moiety of the chemically modified sophorolipid is unsaturated. For example, when the biomass contains unsaturated fatty acids (e.g., oleic acid, linoleic acid), the chemically modified sophorolipids may have an unsaturated aliphatic moiety. The unsaturated aliphatic moiety of a chemically modified sophorolipid may be, in certain embodiments, one to twenty-four carbon atoms, five to twenty-four carbon atoms, five to eighteen carbon atoms, or fifteen to eighteen carbon atoms in length. In other embodiments, the unsaturated aliphatic moiety of a chemically modified sophorolipid is five to seventeen carbon atoms in length. In one embodiment when the aliphatic moiety of the chemically modified sophorolipid is unsaturated, the chain length has an even number of carbon atoms, e.g., sixteen or eighteen carbon atoms in length. In other embodiments, the unsaturated aliphatic moiety is a monounsaturated aliphatic moiety (e.g., a monounsaturated fatty acid, or a monounsaturated fatty alcohol). In yet other embodiments, the unsaturated aliphatic moiety is a polyunsaturated aliphatic moiety (e.g., a polyunsaturated fatty acid, or a polyunsaturated fatty alcohol). In yet other embodiments, the unsaturated aliphatic moiety has two or more, three or more, or four or more unsaturated bonds.

In other embodiments, the aliphatic moiety of the chemically modified sophorolipid mixture is saturated. For example, when the biomass contains saturated fatty acids (e.g., palmitic acid, stearic acid), the chemically modified sophorolipids may have a saturated aliphatic moiety. The saturated aliphatic moiety of a chemically modified sophorolipid may be, in certain embodiments, one to twenty-four carbon atoms, five to twenty-four carbon atoms, five to eighteen carbon atoms, or fifteen to eighteen carbon atoms in length. In one embodiment when the aliphatic moiety of the chemically modified sophorolipid is saturated, the chain length has an odd number of carbon atoms, e.g., fifteen or seventeen carbon atoms in length.

Further, it should be understood that the fatty acid or fatty alcohol chain may be connected to sophorose in various ways to form the sophorolipid compound, such that the fatty acid or fatty alcohol chain may be unbranched (when connected to the terminal carbon of the chain) or branched (when connected to, for example, the C16 or C17 carbon of a C18 chain).

In certain embodiments, one or more monoacetylated acidic sophorolipids makes up at least 5%, at least 10%, at least 25%, at least 50%, at least 75%, at least 90%, or at least 95% by weight of the chemically modified sophorolipid composition described herein. In other embodiments, one or more monoacetylated acidic sophorolipids makes up between 5% and 90%, between 5% and 50%, between 5% and 10%, or between 5% and 7% by weight of the chemically modified sophorolipid composition described herein.

In certain embodiments, one or more sophorolipid esters makes up less than 0.5%, less than 0.25%, less than 0.1%, or less than 0.01% by weight of the composition by weight of the chemically modified sophorolipid composition described herein. In other embodiments, one or more sophorolipid esters makes up at least 0.5%, at least 1%, at least 5%, at least 10%, at least 20%, at least 30%, at least 40%, at least 50%, at least 60%, at least 70%, at least 80%, at least 90%, at least 95%, at least 99% by weight of the chemically modified sophorolipid composition described herein. In yet other embodiments, one or more sophorolipid esters makes up between 0.5% and 99%, between 10% and 90%, or between 50% and 80% by weight of the chemically modified sophorolipid composition described herein.

In other embodiments, less than 5% and 15% by weight of the chemically modified sophorolipid composition are the deacetylated acidic and lactonic sophorolipids, respectively. In yet other embodiments, less than 50% and 20% by weight of the chemically modified sophorolipid composition are monoacetylated and diacetylated lactonic sophorolipids, respectively.

Uses of the Chemically Modified Sophorolipids

One or more of the chemically modified sophorolipids described herein, or any compositions thereof, can be used as inducers that cause cells to produce large amounts of enzymes or other substances than they would otherwise produce if the inducer was absent.

In one aspect, one or more of the chemically modified sophorolipids described herein, or any compositions thereof, can be used for inducing protein production (e.g., cellulase production) in host organisms capable of producing cellulase. For example, in certain embodiments, one or more sophorolipid esters with a structure of formula (II), (IIa), (IIb), (IIc) or (IId), or any compositions thereof, can be used to induce protein production. Examples of such organisms include filamentous fungi, which have the ability to use cellulose by producing cellulases that can hydrolyze the beta-(1,4)-linked glycosidic bonds of cellulose to produce glucose.

Filamentous fungi may include all filamentous forms of the subdivision Eumycotina. See, Alexopoulos, C. J. (1962), INTRODUCTORY MYCOLOGY, Wiley, New York. These fungi are usually characterized by a vegetative mycelium with a cell wall composed of chitin, cellulose, and other complex polysaccharides. Suitable species of filamentous fungi for use with the chemically modified sophorolipids described herein include, for example, hosts selected from the following genera: *Trichoderma, Humicola, Pleurotus, Fusarium, Aspergillus, Streptomyces, Thermomonospora, Bacillus, Cellulomonas, Penicillium, Basidiomycete, Chrysoporium, Pestalotiopsis, Neurospora, Cephalosporium, Achlya, Podospora, Endothia, Mucor, Cochliobolus,* and *Pyricularia.* Specific hosts may include, for example, *Trichoderma reesei* (QM 9414, MCG 77, MCG 80, Rut-C30, CL-847, VTT-D, SVG, and RL-P37) (see Esterbauer et al., *Bioresource Technology,* 36(1):51-65, (1991)), *Penicillium decumbens, Penicillium funiculosum, Penicillium purpurogenum,* and *Chrysosporium lucknowense.*

In some embodiments, one or more of the chemically modified sophorolipids described herein, or any compositions thereof, are used to induce protein production (e.g., cellulase production) in a host cell that is a member of the species of *Trichoderma, Penicillium, Chrysosporium, Humicola, Pleurotus, Fusarium, Aspergillus, Streptomyces, Thermomonospora, Bacillus* or *Cellulomonas.* In certain embodiments, one or more chemically modified sophorolipids, or any compositions thereof, are used to induce protein production (e.g., cellulase production) in a host cell that is a member of the species of *Trichoderma.* In one embodiment, one or more chemically modified sophorolipids, or any compositions thereof, are used to induce protein production (e.g., cellulase production) in *Trichoderma reesei* or *Trichoderma viride.* The term "*Trichoderma*" refers to any fungal genus previously or currently classified as *Trichoderma.* In certain embodiments, the one or more chemically modified sophorolipids is one or more sophorolipid esters with a structure of formula (II), (IIa), (IIb), (IIc) or (IId).

It should also be understood that the chemically modified sophorolipids described herein, or any compositions thereof, may be used with genetically engineered host cells. To produce proteins with recombinant DNA technology, a DNA construct that includes the nucleic acid encoding the amino acid sequence of the designated protein can be constructed and transferred into, for example, a *Trichoderma reesei* host cell. The vector may be any vector known in the art which when introduced into a *Trichoderma reesei* host cell can be integrated into the host cell genome and can be replicated. The nucleic acid encoding the protein can be operably linked to a suitable promoter, which shows transcriptional activity in *Trichoderma reesei* host cell. Suitable promoters may include, for example, cellobiohydrolase 1 (cbh1), endoglucanase, and xylanase. In one exemplary embodiment, the chemically modified sophorolipids described herein, or any compositions thereof, may be a powerful inducer of the cbh1 promoter in *Trichoderma,* which may increase cellulase production by several folders compared to other known cellulase inducers.

It should be understood, however, that the chemically modified sophorolipids described herein, or any compositions thereof, may induce production of any protein that may be under the control of a native or engineered promoter, such as cbh1. The promoter may be derived from genes encoding proteins that may be either homologous or heterologous to the host cell. One of skill in the art would recognize that these promoters can be engineered to enhance its function and the applicability of this new inducer should not be constrained by its alteration. Homologous or heterologous protein expression under this promoter may be routinely carried out using recombinant molecular biology techniques known in the art, which may rely on successful recombination of genes encoding the protein of interest. Examples of homologous and heterologous proteins of interest include, for example, enzymes, hormones, growth factors, cytokines, vaccines, antibodies, and polypeptides. In some embodiments, the chemically modified sophorolipids described herein may induce production of enzymes including, for example, cellulases, amylases, proteases, xylanases, lipases, esterases, phytases, pectinases, catalases, pullulanases, laccases, oxidases, glucose isomerases, lyases, acylases, and transferases.

Fermentation procedures for production of proteins are generally known to one of skill in the art. Generally, cells are cultured in a medium containing physiological salts and nutrients. See, e.g., Pourquie, J. et al., BIOCHEMISTRY AND GENETICS OF CELLULOSE DEGRADATION, eds. Aubert, J. P. et al., Academic Press, pp. 71-86, 1988; and Ilmen, M. et al., *Appl. Environ. Microbiol.* 63:1, 298-1306 (1997). For example, *Trichoderma* cells may be cultured in the medium as described by England et al. in U.S. 2010/0009408. Culture-conditions (e.g., temperature, pH, duration) are also generally known in the art. For example, cultures may be incubated at approximately 28° C. in appropriate medium in shake cultures or fermentors until desired levels of cellulase expression are achieved. After fungal growth has been established, the cells are exposed to conditions effective to cause or permit the expression of the protein.

One or more of the chemically modified sophorolipids described herein, or any compositions thereof, may be added to the medium at a concentration effective to induce protein production (e.g., cellulase production). The chemically modified sophorolipids may also be added to the medium in an insoluble or soluble form. In certain embodiments, the chemically modified sophorolipids can be reconstituted in water or one or more solvents (e.g., ethanol, dimethyl sulfoxide, or ethyl acetate) prior to the introduction into the fermentation culture as a media component or as inducing feed. Solubilizing the chemically modified sophorolipids allows for their use as a concentrated feed for protein production in an industrial fed-batch fermentation process. Further, it should be understood that the chemically modified sophorolipids may be used in either a batch or a continuous fermentation process.

The use of one or more of the chemically modified sophorolipids described herein has been found to surprisingly increase cellulase production by several folds compared to a natural sophorolipid mixture, and known inducers such as sophorose, cellobiose and lactose. In certain embodiments, the use of one or more of the chemically modified sophorolipids described herein, or any compositions thereof, can increase cellulase production in a *Trichoderma* host (e.g., *Trichoderma reesei*) by at least two folds, by at least four folds, or by at least five folds compared to a natural sophorolipid mixture. In other embodiments, the use of one or more of the chemically modified sophorolipids described herein, or any compositions thereof, can increase cellulase production in a *Trichoderma* host (e.g., *Trichoderma reesei*) by between two to five folds compared to the use of a natural sophorolipid mixture. It should be understood that, in one variation, the natural sophorolipid mixture is the one from which the one or more chemically modified sophorolipids, or any compositions thereof, were prepared. In other embodiments, the chemically modified sophorolipids described herein, or any compositions thereof, can increase cellulase production in a *Trichoderma* host (e.g., *Trichoderma reesei*) by at least ten folds, by at least twenty folds, or by at least thirty folds compared to cellobiose or lactose. In certain embodiments, the one or more chemically modified sophorolipids is one or more sophorolipid esters with a structure of formula (II), (IIa), (IIb), (IIc) or (IId).

The individual compounds of the chemically modified sophorolipid composition may also have different protein induction abilities. For example, the sophorolipids esters in the chemically modified sophorolipid composition have surprisingly been observed to have greater cellulase induction abilities in *Trichoderma* than the other components of the chemically modified sophorolipid composition. Thus, while the chemically modified sophorolipid composition can be used to induce protein production in a host cell, it should also be understood that the individual components of the chemically modified sophorolipid composition can be individually separated or isolated, and optionally further purified.

For example, in some embodiments, one or more sophorolipid esters may be isolated for use in protein production in *Trichoderma*. In some embodiments, the use of one or more sophorolipid esters isolated from a chemically modified sophorolipid composition may result in at least a twenty-fold, at least a thirty-fold, at least a forty-fold, at least a fifty-fold, or at least a hundred-fold increase in cellulase production in *Trichoderma* compared to the use of a natural sophorolipid mixture. In other embodiments, the use of one or more sophorolipid esters isolated from a chemically modified sophorolipid composition results in between a twenty-fold to a hundred-fold increase in cellulase production in *Trichoderma* compared to a natural sophorolipid mixture. It should be understood that, in one variation, the natural sophorolipid mixture is the one from which the chemically modified sophorolipid composition was prepared.

In other embodiments, the use of one or more sophorolipid esters isolated from a chemically modified sophorolipid composition may result in at least a two-fold, at least a three-fold, at least a four-fold, at least a five-fold, at least a nine-fold, at least a ten-fold increase, at least a twenty-fold increase, or at least a twenty five-fold increase in cellulase production in *Trichoderma* compared to the use of sophorose. In other embodiments, the use of one or more sophorolipid esters isolated from a chemically modified sophorolipid composition may result in between a five-fold to a ten-fold increase compared to the use of sophorose.

In particular embodiments, the use of a monoacetylated sophorolipid ester that is isolated from a chemically modified sophorolipid composition results in at least a ten-fold, at least a twenty-fold, at least a thirty-fold, at least a forty-fold, at least a fifty-fold, at least a hundred-fold, at least a two hundred-fold, or at least a two hundred fifty-fold increase in cellulase production in *Trichoderma* compared to a natural sophorolipid mixture. It should be understood that, in one variation, the natural sophorolipid mixture is the one from which the monoacetylated sophorolipid ester was prepared. In other embodiments, the use of monoacetylated sophorolipid ester that is isolated from a chemically modified sophorolipid composition results in at least a two-fold, at least three-fold, at least a four-fold, at least a five-fold, or at least a ten-fold, or at least a twenty-fold, at least a thirty-fold, at least a forty-fold, or at least a fifty-fold increase in cellulase production in *Trichoderma* compared to sophorose.

In particular embodiments, the use of a deacetylated sophorolipid ester that is isolated from a chemically modified sophorolipid composition results in at least a ten-fold, at least a twenty-fold, at least a thirty-fold, at least a forty-fold, at least a fifty-fold, at least a sixty-fold, at least a seventy-fold, at least an eighty-fold, at least a ninety-fold, or at least a hundred-fold increase in cellulase production in *Trichoderma* compared to a natural sophorolipid mixture. It should be understood that, in one variation, the natural sophorolipid mixture is the one from which the deacetylated sophorolipid ester was prepared. In other embodiments, the use of deacetylated sophorolipid ester that is isolated from a chemically modified sophorolipid composition results in at least a two-fold, at least three-fold, at least a five-fold, or at least ten-fold increase in cellulase production in *Trichoderma* compared to sophorose.

In one embodiment, the use of one or more sophorolipid esters having the structure of formula (II), (IIa), (IIb), (IIc) or (IId), or a combination thereof, that is isolated from a chemically modified sophorolipid composition results in at least a ten-fold, at least a twenty-fold, at least a thirty-fold, at least a forty-fold, at least a fifty-fold, at least a hundred-fold, at least a two hundred-fold, or at least a two hundred fifty-fold increase in cellulase production in *Trichoderma* compared to a natural sophorolipid mixture. It should be understood that, in one variation, the natural sophorolipid mixture is the one from which the one or more sophorolipid esters having the structure of formula (II), (IIa), (IIb), (IIc) or (IId) was prepared. In other embodiments, the use of one or more sophorolipid esters having the structure of formula (II), (IIa), (IIb), (IIc) or (IId) that is isolated from a chemically modified sophorolipid composition results in a two-fold, at least three-fold, at least a four-fold, at least a five-fold, or at least a ten-fold, or at least a twenty-fold, at least a twenty-five fold, or at least a thirty-fold increase in cellulase production in *Trichoderma* compared to sophorose.

Method of Preparing Chemically Modified Sophorolipids

Provided herein are also methods of producing sophorolipids by chemically modifying a natural sophorolipid mixture. Several methods are currently known in the art for chemically modifying sophorolipids including, for example, alkaline hydrolysis and ozonolysis. See e.g., Rau et al., *Industrial Crops and Products*, 13:85-92 (2001); and EP 0710158.2.

In one aspect, the methods described herein involve chemically modifying a natural sophorolipid mixture by acid hydrolysis. When a natural sophorolipid mixture is treated under acidic conditions at elevated temperatures, a chemically modified sophorolipid composition is obtained. This chemically modified sophorolipid composition has been observed to be highly inductive to protein production (e.g., cellulase production) in filamentous fungi host cells (e.g., *Trichoderma*), exceeding the inductive ability of other known cellulase inducers such as sophorose, lactose and cellobiose.

a) Natural Sophorolipid Mixture

The natural sophorolipid mixture used to prepare the chemically modified sophorolipids can be produced by yeast. Suitable yeast strains may be selected from, for example, the following genera: *Candida*, *Starmerella*, *Rhodotorula*, and *Wickerhamiella*. Specific strains suitable for sophorolipid production include, for example, *Candida bombicola* (e.g., ATCC 22214, NRRL Y-30816), *Starmerella bombicola*, *Candida apicola*, *Candida riodocensis*, *Candida stellata*, and *Candida* sp. NRRL Y-27208. See Kurtzman et al., "Production of sophorolipid biosurfactants by multiple species of the *Starmerella* (*Candida*) *bombicola* yeast clade", *FEMS Microbiol. Lett.*, 311: 140-146 (2010).

In some embodiments, the natural sophorolipid mixture is produced by the yeast *Candida bombicola* or *Candida apicola*. For example, *Candida bombicola* has an active extracellular lipase system that first cleaves triglycerides from vegetable oil into free fatty acids, which are readily taken up by the yeast. The fatty acids then undergo hydroxylation at the ultimate or penultimate carbon through the action of cytochrome P450. Sophorose is then added onto the hydroxylated fatty acid by the actions of two glycosyltransferases. See Fleurackers, S. J. J., *Eur. J. Lipid Sci. Technol.*, 108:5-12 (2006). Acetylation and lactonization complete the formation of sophorolipids, which are then secreted by the yeast.

Fermentation procedures for production of sophorolipids are generally known to one of skill in the art. Suitable carbon substrates used in the fermentation to produce the natural sophorolipids may include hydrophobic substrates, for example, vegetable oils (e.g., canola, soy, corn, palm, coconut, sunflower seed, cottonseed, or olive oils), fatty acids (e.g., palmitic, oleic, elaidic, linoleic, alpha-linolenic, or stearic acids), fatty acid esters (e.g., fatty acid methyl ester or fatty acid ethyl ester), alkanes (e.g., pentadecane, hexadecane, heptadecane, or octadecane), and fatty alcohols (e.g., pentadecanol, hexadecanol, heptadecanol, or octadecanol).

The length of the carbon substrates used in the fermentation to produce the natural sophorolipids may depend on the fermentation host. For example, in certain embodiments where a *Candida* host (e.g., *Candida bombicola*) is used, the fatty acids and/or alkanes have a chain length of between fifteen and eighteen carbon atoms. In one variation, fatty acids with carbon chains of between fifteen and eighteen carbon atoms may be preferable to alkanes with carbon chains of between fifteen and eighteen carbon atoms. See Van Bogaert et al., *Process Biochemistry*, 46(4): 821-833 (2011). In one embodiment, the carbon substrate used in the fermentation to produce the natural sophorolipids is canola oil, which has a high C18 content and a monounsaturated fatty acid chain. Further, it should also be understood that other longer or shorter carbon substrates can be used, but can be reduced or elongated to between 15 and 18 carbon chains for use with a *Candida* host.

Figure 1:
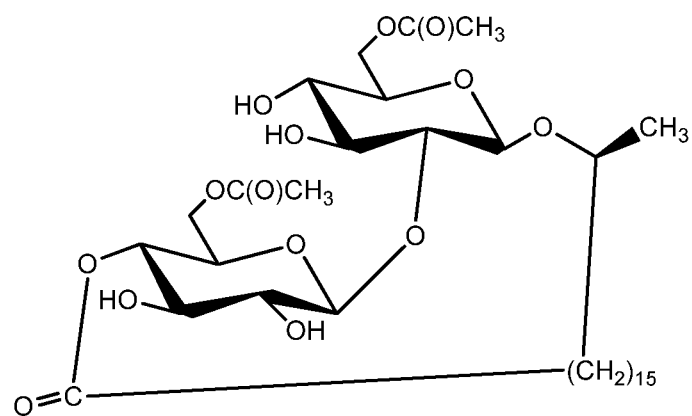
FIG. 1 depicts the chemical structures of two natural sophorolipids produced by *Candida bombicola*: (A) diacetylated lactonic sophorolipid; and (B) diacetylated acidic sophorolipid.
Figure 1:
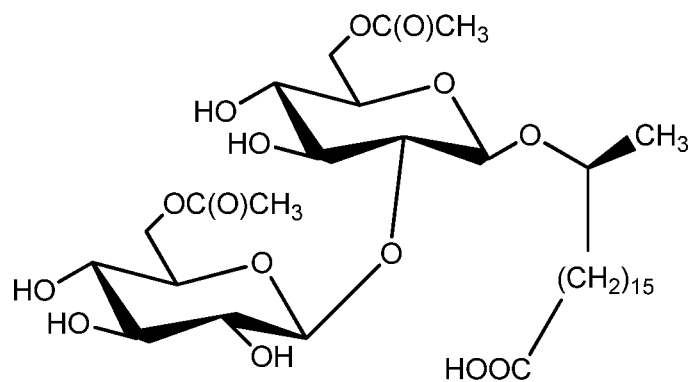

Yeast typically produces a mixture sophorolipids, and the sophorolipid molecules of the mixture usually have one sophorose molecule linked to a hydroxylated fatty acid at the C1' position of the sophorose molecule. The natural sophorolipid mixture may include diacetylated sophorolipids in either lactonic or acidic forms. Exemplary diacetylated lactonic and diacetylated acidic sophorolipids are depicted in FIG. 1.

For natural sophorolipid mixtures produced by *Candida bombicola*, diacetylated lactonic sophorolipids are typically present in a greater amount (e.g., greater than 60%) than acidic sophorolipids (e.g., less than 10%). See Asmer et al., "Microbial production, structure elucidation and bioconversion of sophorose lipids", *J. Am. Oil Chem. Society*, 65(9): 1460-1466 (1988); Davila et al., "Identification and determination of individual sophorolipids in fermentation products by gradient elution high-performance liquid chromatography with evaporative light-scattering detection", *Journal of Chromatography*, 648:139-149 (1993); Davila et al., "Sophorose lipid production from lipidic precursors: predictive evaluation of industrial substrates", *J. Indust. Microbiology*, 13: 249-257 (1994); Ratsep & Shah, "Identification and quantification of sophorolipid analogs using ultra-fast liquid chromatography-mass spectrometry", *J. Microbiological Methods*, 78: 354-356 (2009).

With reference again to FIG. 1, the sophorolipids of the natural sophorolipid mixture typically have acetyl groups at the C6'' and/or C6' positions of the sophorose molecule. See Van Bogaert et al., *Process Biochemistry*, 46(4):821-833 (2011). The fatty acid groups may be saturated or unsaturated, and may vary in length. Typically, sophorolipids in a natural sophorolipid mixture have a fatty acid chain of sixteen to eighteen carbon atoms.

The composition of the natural sophorolipid mixture may depend on the type of feedstock and culture conditions. For example, if the feedstock is a fatty acid ester rather than vegetable oil or free fatty acids, more of the free acidic sophorolipids may be produced. See Ashby et al., U.S. 2006/0199244.

b) Acid Treatment of the Natural Sophorolipid Mixture

Natural sophorolipids can be chemically modified by acid hydrolysis, which leads to deacetylation and ring opening of the natural sophorolipids. The acids suitable to hydrolyze the natural sophorolipid mixture may include, for example, hydrochloric acid, sulfuric acid or nitric acid. In some embodiments, a mixture of acids may also be used.

In some embodiments, the acid treatment is performed at elevated temperatures. In certain embodiments, the acid hydrolysis may be performed at a temperature of at least 50° C. In other embodiments, the acid hydrolysis may be performed at a temperature of at least 80° C., at least 90° C., at least 100° C., or at least 110° C. In other embodiments, the acid hydrolysis may be performed at a temperature between 50° C. and 120° C., or between 100° C. and 120° C. The natural sophorolipid mixture can be contacted with the acid at elevated temperatures for a range of time, e.g., from minutes to hours.

c) Isolation and Purification

The methods described herein to acid hydrolyze a natural sophorolipid mixture typically yields a mixture of chemically modified sophorolipids that can be isolated as a floc. Any solid/liquid separation techniques known in the art may be employed to isolate the floc, including, for example, sedimentation, filtration, or centrifugation.

The isolated precipitate can be purified to separate the individual sophorolipids that make up the chemically modified sophorolipid composition. Suitable purification methods may include, for example, chromatography, adsorption, extraction, re-precipitation, and crystallization.

EXAMPLES

The following examples are intended only to further illustrate the invention and are not intended to limit the scope of the invention as defined by the claims.

Example 1

Preparation of a Natural Sophorolipid Mixture

*Candida bombicola* (ATCC 22214) was selected as the sophorose-producing host in this Example. The freeze-dried stock inside a glass vial was transferred into a yeast extract, peptone, dextrose (YPD) culture broth, and grown for 48 hours at 28° C. for two days. The culture was then mixed with sterilized glycerol to prepare a final culture containing 20% glycerol. A cell bank was then established using cryovials with 1 mL of seed culture each, and stored at −80° C.

For the production of natural sophorolipids from canola oil, a production medium was first prepared and included the following components: 100 g/L glucose, 10 g/L yeast extract, 1 g/L urea, and 100 g/L canola oil (Crisco, Pure Canola). Based on the data provided from the manufacturer, the canola oil has 64% monounsaturated fat from mainly oleic fatty acid, and 29% polyunsaturated fat from mainly linoleic and alpha-linolenic fatty acids.

To initiate the fermentation, a 1 mL seed from a cryovial was placed into 50 mL of production medium inside a 250 mL baffled flask incubated at 28° C. and 250 revolutions per minute (RPM). After seven days, sophorolipids appeared in the media as a viscous brown phase. Since the viscous brown phase was heavier than water, this brown phase was isolated using a separation funnel, with heating at about 60° C. to aid the separation. The isolated brown phase contained the natural sophorolipid mixture, as well as residual fatty acids from undigested canola oil. The natural sophorolipid mixture was then mixed with three volumes of ethanol and centrifuged at 4,000 RPM for 10 minutes to remove the residual yeast. The ethanol and water were then evaporated under vacuum, after which the natural sophorolipid mixture appeared as a yellow oily residue. Approximately 2.5 g of the natural sophorolipid mixture was recovered from each 50 mL culture. The dry weight of the natural sophorolipid mixture was determined to be about 59%, with a density of about 1.11 g/mL.

When analyzed by liquid chromatography-mass spectrometry (LC-MS), the natural sophorolipid mixture was observed to include a mixture of acetylated lactonic and acidic sophorolipids.

Example 2

Acid Treatment of the Natural Sophorolipid Mixture

Acid hydrolysis was carried out on the natural sophorolipid mixture prepared according to the procedure described in Example 1 above. 0.25 mL of the natural sophorolipid mixture was mixed into 4.75 mL of a 0.1N hydrochloric acid (HCl) solution inside a 15 mL centrifuge tube. The tube was first vortexed to generate an emulsion, and then placed under boiling water (about 100° C.) for two hours. The emulsion was observed to turn into a yellow oily phase due to the low solubility of sophorolipids at a low pH. After two hours, the tube was agitated, and then cooled under cold tap water and a white to light yellow colored precipitate was observed to gradually form.

When analyzed by LC-MS, the acid treatment of the natural sophorolipid mixture was observed to yield partial hydrolysis of the natural sophorolipid mixture. The acid-treated product mixture was observed to include glucose, sophorose, acetic acid, free fatty acids, as well as a precipitate made up of fully and partially deacetylated sophorolipids (in both lactonic and acidic forms) and glucolipids. The glucose and sophorose were produced due to the non-specific hydrolytic reactions.

Example 3

Alkaline Treatment of the Natural Sophorolipid Mixture

Alkaline hydrolysis was carried out on the natural sophorolipid mixture prepared according to the procedure described in Example 1 above. The alkaline treatment employed a similar procedure as the acid treatment described in Example 2 above, except the 0.1N HCl was replaced by 0.1N sodium hydroxide (NaOH). The sophorolipids were completely solubilized under alkaline conditions, and no precipitate was observed after 2 hours of reaction under heat.

When analyzed by LC-MS, the alkaline treatment of the natural sophorolipid mixture was observed to yield a complete hydrolysis of the natural sophorolipid mixture. The alkaline-treated product mixture was observed to include solubilized and fully deacetylated acidic sophorolipid. See also Rau et al., *Industrial Crops and Products*, 13:85-92, (2001).

Example 4

Cellulase Induction Studies in *Trichoderma reesei*

*Trichoderma reesei* (Rut-C30) was selected as the host for cellulase expression in this Example. To prepare for the cellulase induction studies, a citrate minimal media was first prepared. The media composition described by England et al. in U.S. 2010/0009408 was modified to include 14.4 g/L citric acid, 4 g/L $KH_2PO_4$, 6.35 g/L $(NH_4)_2SO_4$, 2 g/L $MgSO_4$-$7H_2O$, 0.53 g/L $CaCl_2$-$2H_2O$, and trace metal elements at 1 mL/L, which included 5 g/L $FeSO_4$-$7H_2O$, 1.6 g/L $MnSO_4$—$H_2O$, and 1.4 g/L $ZnSO_4$-$7H_2O$. The final pH was adjusted to 5.50 using NaOH.

The *Trichoderma reesei* (ATCC 56765) was used in this Example. This fungal strain was developed as a catabolic de-repressed strain from classic mutagenesis of parent strain NG14 and the wild type QM6A. See Seidl et al., *BMC Genomics*, 9:327 (2008). To propagate *Trichoderma*, the freeze-dried stock from ATCC was first dissolved in sterile deionized water, and then transferred onto a potato dextrose agar (PDA) plate (Teknova P0047) using a sterile loop. The PDA plate was maintained at room temperature under white fluorescent light. After approximately seven days, green *Trichoderma* spores were observed. In addition, 60% (w/v) glucose, 15% (w/v) lactose, and 15% (w/v) cellobiose stocks were prepared and used both as controls and as the carbon source for *Trichoderma* growth.

To initiate cellulase induction studies for each of the sophorolipid mixtures prepared in Examples 1-3 above, 0.5 mL of glucose stock was first placed into 14 mL of citrate minimal media inside a 125 mL baffled flask. To this culture was added 0.5 ml of the precipitate containing the natural sophorolipid mixture (from Example 1), the precipitate containing the acid-treated sophorolipid mixture (from Example 2), and the solution containing the alkaline-treated sophorolipid mixture (from Example 3). Both the natural sophorolipid and acid-treated sophorolipid precipitates were washed with sterile deionized water to remove residual free sophorose before addition to the culture. At 0.5 mL addition, the final sophorolipid concentration was calculated to be approximately 1.1 g/L, although the acid-treated sophorolipid mixture may have had a value less than the 1.1 g/L due to possible hydrolytic actions.

For the glucose control (with no inducer), 0.5 mL of glucose stock was placed into 14.5 mL minimal media, resulting in a final glucose concentration of about 2%. For the lactose and cellobiose experiments, 2 mL of stock was added to 13 mL of media, resulting in a final concentration of about 2%.

To commence the fermentation, an approximately 1 cm×1 cm square agar plug was removed from the *Trichoderma* spore-containing PDA agar plate using a sterile loop and placed into the cellulase induction culture media. The cultures were placed inside a 28° C. incubator with shaking at 250 RPM. At five days of fermentation, the samples were collected and analyzed for carboxymethylcellulose (CMC) endo-glucanase activity. Since the *Trichoderma reesei* Rut-C30 is a cellulase hyper-producer, the CMC activity directly correlates with the amount of protein being induced. The CMC activity assay followed a procedure modified from Mandels and Reese using a 0.3 mL reaction volume. See Mandels and Reese, *J. Bacteriol.*, 73:269-278 (1957). It should be understood that one CMC unit denotes the activity that liberates 1 mmol of reducing sugars (expressed as glucose equivalents) in one minute under the specified conditions of 50° C. and pH 4.8. Table 1 below summarizes the results for the CMC activity assays in this Example.

TABLE 1

Results for CMC activity assays

| Induction media | CMC (U/mL) at day 5 |
| --- | --- |
| Glucose control (2%) | 1.19 |
| Cellobiose control (2%) | 2.05 |
| Lactose control (2%) | 10.1 |
| Glucose (2%) + 1.1 g/L natural sophorolipid (washed) | 2.91 |
| Glucose (2%) + 1.1 g/L alkaline treated sophorolipid | 1.44 |
| Glucose (2%) + 1.1 g/L precipitate of acid treated sophorolipid (washed) | 12.3 |

The cellobiose, the natural sophorolipid mixture, and the alkaline-treated sophorolipid mixture were observed to have marginal cellulase activity compared to the glucose control. On the other hand, the acid-treated sophorolipid mixture was observed to have a ten-fold higher induction than the natural sophorolipid mixture and glucose control. The induction from the acid-treated sophorolipid mixture was observed to exceed the induction from 2% lactose with only 1.1 g/L precipitate added to a 2% glucose background. For all the cultures tested, the cell mass was not determined although the packed cell volumes were similar.

Example 5

Concentration Effects of the Acid-Treated Sophorolipid Mixture on Cellulase Induction 1 mL, 0.5 mL, and 0.25 mL of acid-treated sophorolipid mixtures were prepared according to the procedure described in Example 2. The acid-treated sophorolipid mixture was isolated as a precipitate by centrifugation, and then washed with sterile deionized water. The isolated acid-treated sophorolipid mixture was reconstituted in 0.5 mL sterile water prior to use in the *Trichoderma reesei* culture. The concentrations of the acid-treated sophorolipid mixture from the 1 mL, 0.5 mL, and 0.25 mL collections used in the cellulase induction studies were 2.2 g/L, 1.1 g/L, and 0.55 g/L, respectively. Cellulase induction studies were performed according to the procedures described in Example 4 above. Table 2 below summarizes the results for the CMC activity assays in this Example.

TABLE 2

Results for CMC activity assays

| Induction media | CMC (U/mL) at day 5 |
| --- | --- |
| Glucose control (2%) | 0.22 |
| Lactose control (2%) | 8.29 |
| Glucose (2%) + 2.2 g/L precipitate of acid treated sophorolipid (washed) | 16.7 |
| Glucose (2%) + 1.1 g/L precipitate of acid treated sophorolipid (washed) | 9.15 |
| Glucose (2%) + 0.55 g/L precipitate of acid treated sophorolipid (washed) | 4.89 |

The cellulase induction from acid-treated sophorolipid mixture was observed to be concentration dependent. As seen in Table 2 above, doubling the concentration of the acid-treated sophorolipid almost doubled the cellulase induction (about a 1.8-fold increase).

Example 6

Solvent Effects of Solubilized Acid-Treated Sophorolipid Mixture on Cellulase Induction An acid-treated sophorolipid mixture was prepared according to the procedure described in Example 2. The acid-treated sophorolipid mixture was isolated as a precipitate by centrifugation, and then washed with sterile deionized water.

Prior to use in a *Trichoderma* culture for cellulase induction studies, the acid-treated sophorolipid mixture was reconstituted in (a) sterile water, (b) 10% ethanol, and (c) 5% dimethyl sulfoxide (DMSO). The acid-treated sophorolipid mixture was observed to be insoluble in water at low pH; however, the acid-treated sophorolipid mixture was observed to dissolve in ethanol and DMSO.

Cellulase induction studies were performed according to the procedures described in Example 4 above. Table 3 below summarizes results from the CMC activity assays in this Example.

TABLE 3

Results for CMC activity assays

| Induction media | Solvent used for reconstitution | CMC (U/mL) at day 5 |
| --- | --- | --- |
| Glucose control (2%) | | 0.28 |
| Glucose (2%) + 1.1 g/L precipitate of acid treated sophorolipid (washed) | Sterile water | 8.05 |
| Glucose (2%) + 1.1 g/L precipitate of acid treated sophorolipid (washed) | 10% Ethanol | 9.94 |
| Glucose (2%) + 1.1 g/L precipitate of acid treated sophorolipid (washed) | 6% DMSO | 10.7 |

Reconstituting the acid-treated sophorolipid mixture in ethanol and DMSO was observed to have comparable efficacy in inducing cellulase production in *Trichoderma* compared to reconstituting the acid-treated sophorolipid mixture in water. While ethanol and DMSO was observed to slightly delay cell growth at the start of culture, cell growth recovered after two days. Since the acid-treated sophorolipid mixture can be solubilized in solvents such as ethanol and DMSO, the acid-treated sophorolipid mixture can be prepared as a concentrated feed for the cellulase production in industrial fed-batch fermentation processes.

Example 7

Comparison of Cellulase Induction Using Various Acid-Treated Sophorolipid Mixtures Versus Alkaline-Treated Sophorolipid Mixtures Natural sophorolipid mixtures were prepared according to the procedure described in Example 1 above. The natural sophorolipid mixtures were independently treated using sulfuric acid ($H_2SO_4$), hydrochloric acid (HCl) and sodium hydroxide (NaOH).

For the acidic treatments, a 0.1M $H_2SO_4$ solution and a 0.1N HCl solution were used. A acid treatment procedure similar to the one described in Example 2 above was performed, except these acidic reactions in this Example were autoclaved at 120° C. for thirty minutes. A precipitate was observed in each of these reactions.

For the alkaline treatment, a 0.1N NaOH solution was used. An alkaline treatment procedure similar to the one described in Example 3 above was performed, except the reaction was carried out for fifteen minutes instead of two hours. The pH was also reduced to 8.0 from the initial pH of 13.0.

Cellulase induction studies were performed according to the procedures described in Example 4 for each of the acid-treated and alkaline-treated sophorolipid mixtures prepared in this Example. Table 4 below summarizes the results for the CMC activity assays in this Example.

TABLE 4

Results for CMC activity assays

| Induction media | Sophorolipid treatment condition | CMC (U/mL) at day 5 |
|---|---|---|
| Glucose control (2%) | | 0.22 |
| Glucose (2%) + 1.1 g/L precipitate of acid (HCl) treated sophorolipid (washed) | 0.1N HCl, 120° C., 30 minutes | 12.5 |
| Glucose (2%) + 1.1 g/L precipitate of acid ($H_2SO_4$) treated sophorolipid (washed) | 0.1M $H_2SO_4$, 120° C., 30 minutes | 10.8 |
| Glucose (2%) + 1.1 g/L partially alkaline treated sophorolipid | 0.1N NaOH, 100° C., 15 minutes | 2.66 |

Both acid-treated sophorolipid mixtures were observed to have greater induction than the alkaline-treated sophorolipid mixture. As seen in Table 4 above, the use of the acid-treated sophorolipid mixture resulted in a four- to five-fold increase in cellulase induction compared to the alkaline-treated sophorolipid mixture.

Example 8

Cellulase Induction Studies Using an Acid-Treated Sophorolipid Mixture

A natural sophorolipid mixture was produced by *Candida bombicola* according to the procedure described in Example 1 above. The natural sophorolipid mixture was then hydrolyzed by hydrochloric acid according to the procedure described in Example 2. The acid-treated sophorolipid mixture was then isolated as a precipitate by centrifugation, and was then purified and fractionated by flash chromatography. A silica gel column (Fisher, 230-400 Mesh), with methylene chloride/methanol as the mobile phase, was used. Fractions (about 5 mL each) were collected in culture tubes. Fractions containing the product with mass 687 $[M+Na]^+$ were combined. The other fractions obtained from column chromatography were also combined, and further purified using reverse phase HPLC (Agilent ZORBAX eclipse XDB C18, 4.6×250 mm, 5 µm) with acetonitrile/water as the mobile phase.

Several fractions were separated from the acid-treated sophorolipid mixture, but four isolated fractions in particular were observed to have significant cellulase inductive power. These four isolated fractions (labeled fractions 1-4), as well as the natural sophorolipid mixture produced by *Candida bombicola* and the acid-treated sophorolipid mixture were each analyzed by LC-MS. LC-MS was carried out using a Water 2695 HPLC with Waters ZMD 1000 Mass spectrometer and a Waters 2996 DAD detector. The analysis was conducted using a Waters Symmetry C18 column (4.6×75 mm, 3.5 µm) with acetonitrile and water containing 0.1% trifluoroacetic acid (TFA) as mobile phase on a 5% to 85% acetonitrile gradient for a total run time of 10 minutes.

Cellulase induction studies were performed according to the procedures described in Example 4 above for each of the following: lactose, cellobiose, sophorose, the natural sophorolipid mixture, the acid-treated sophorolipid mixture, and the four fractions isolated from the acid-treated sophorolipid mixture. Table 5 below summarizes the results for the CMC activity assays in this Example.

TABLE 5

Cellulase activity of known inducers versus natural and acid-treated sophorolipids

| | Inducer concentration | | Cellulase activity | |
|---|---|---|---|---|
| Induction media | Mg/15 mL | mM | U/mL at day 3 | U/mg at day 3 |
| glucose control (2%)* | 0 | 0 | 0.28 ± 0.17 | NA |
| lactose (1.0 g/L) | 15 | 2.92 | 0.64 | 0.64 |
| cellobiose (1.0 g/L) | 15 | 2.92 | 0.34 | 0.34 |
| sophorose (0.13 g/L) | 2.0 | 0.38 | 3.58 | 26.9 |
| sophorose (1.3 g/L) | 20 | 3.90 | 15.0 | 11.2 |
| Natural (unmodified) sophorolipid mixture (1.1 g/L)** | 16 | ~1.57 | 2.90 | 2.72 |
| Acid-treated sophorolipid mixture (0.15 g/L)** | 2.2 | ~0.24 | 1.50 | 10.2 |
| Acid-treated sophorolipid mixture (1.1 g/L)** | 16 | ~1.77 | 12.0 | 11.3 |
| Fraction 1 of acid-treated sophorolipid (0.14 g/L)** | 2.1 | ~0.20 | 17.2 | 122.9 |
| Fraction 2 of acid-treated sophorolipid (0.073 g/L)** | 1.1 | ~0.10 | 5.97 | 81.4 |
| Fraction 3 of acid-treated sophorolipid (0.12 g/L)** | 1.8 | ~0.17 | 17.5 | 145.8 |
| Fraction 4 of acid-treated sophorolipid (0.053 g/L)** | 0.8 | ~0.076 | 13.2 | 247.5 |

*All media contain 2% glucose as the carbon source.
**Both the natural and acid-treated sophorolipid mixtures were treated to remove residual sophorose.

As seen in Table 5 above, the acid-treated sophorolipid mixture was observed to have greater induction power than known inducers, lactose and cellobiose, and the natural sophorolipid mixture. The specific induction power of the acid-treated sophorolipid mixture at 1.1 g/L was observed to be an order of magnitude higher than lactose and cellobiose at 1.0 g/L, and at least five times greater than the natural sophorolipid mixture at 1.1 g/L.

Fractions 1-4 isolated from the acid-treated sophorolipid mixture were also observed to be highly inductive, showing cellulase activity greater than the acid-treated sophorolipid mixture, the natural sophorolipid mixture and the known inducers (lactose, cellobiose and sophorose). For example, as seen in Table 5 above, each of the four fractions had specific induction powers that were several hundred times greater than that of lactose and cellobiose. Fraction 1 at 0.14 g/L had a specific induction power that was about four to five times greater than sophorose at 0.13 g/L, and about ten times greater than the natural sophorolipid mixture. Moreover, fractions 2-4 were each observed to have specific induction powers about three, five, and nine times greater than sophorose at 0.13 g/L, respectively, and about thirty to ninety times greater than the natural sophorolipid mixture.

Thus, the acid-treated sophorolipid mixture was observed to contribute to significantly greater cellulase production in *Trichoderma* compared with lactose, cellobiose, sophorose, and the natural sophorolipid mixture from which the acid-treated sophorolipid mixture was derived.

Example 9

Cellulase Induction Studies Using Components of an Acid-Treated Sophorolipid Mixture A natural sophorolipid mixture was produced by *Candida bombicola* according to the procedure described in Example 1 above. The natural sophorolipid mixture was then hydrolyzed by hydrochloric acid according to the procedure described in Example 2. The acid-treated sophorolipid mixture was then isolated as a precipitate by centrifugation, and was then purified and fractionated by flash chromatography. A silica gel column (Fisher, 230-400 Mesh), with methylene chloride/methanol as the mobile phase, was used. Fractions (about 5 mL each) were collected in culture tubes. Fractions were first visualized on TLC plates according to Asmer et al., and then combined based on $R_f$ values. The combined fractions were tested for cellulase induction following the procedures described in Example 4. The combined fractions that are active were further purified using preparative reverse phase HPLC (Waters Prep LC 4000 system, Agilent Eclipse XDB C18 column, 9.4×250 mm, 5 μm) with acetonitrile/water as the mobile phase.

Several fractions were separated from the acid-treated sophorolipid mixture, but two isolated fractions in particular were observed to have significant cellulase inductive power. These two isolated fractions (labeled fractions 1 and 2), as well as the natural sophorolipid mixture produced by *Candida bombicola* and the acid-treated sophorolipid mixture were each analyzed by LC-MS. LC-MS was carried out using a Water 2695 HPLC with Waters ZQ 2000 Mass spectrometer and a Waters 2487 UV detector. The analysis was conducted using a Waters Symmetry C18 column (4.6×250 mm, 5 μm) with acetonitrile and water containing 0.1% formic acid (FA) as mobile phase on a gradient for a total run time of 30 minutes.

Based on the LC-MS analysis, as shown in FIGS. 3A-D, some of the major components of the acid-treated sophorolipid mixture were determined, as summarized in Table 6 below.

TABLE 6

List of major components in acid-treated sophorolipid composition

| Component | Approx. molar mass | $[M + H]^+$ (m/z) |
|---|---|---|
| Deacetylated glucolipid | 460 | 461 |
| Monoacetylated glucolipid | 502 | 503 |
| Deacetylated lactonic sophorolipid | 604 | 605 |
| Deacetylated sophorolipid ester, with fatty alcohol | 622 | 623 |
| Deacetylated acidic sophorolipid | 622 | 623 |
| Monoacetylated lactonic sophorolipid | 646 | 647 |
| Monoacetylated sophorolipid ester, with fatty alcohol | 664 | 665 |
| Monoacetylated acidic sophorolipid | 664 | 665 |
| Diacetylated lactonic sophorolipid | 688 | 689 |
| Diacetylated acidic sophorolipid | 706 | 707 |

Cellulase induction studies were performed according to the procedures described in Example 4 above for each of the following: lactose, cellobiose, sophorose, the natural sophorolipid mixture, the acid-treated sophorolipid mixture, and the two fractions isolated from the acid-treated sophorolipid mixture. Table 7 below summarizes the results for the CMC activity assays in this Example.

TABLE 7

Cellulase activity of known inducers versus natural and acid-treated sophorolipids

| | Inducer concentration | | Cellulase activity | |
|---|---|---|---|---|
| Induction media | Mg/15 mL | mM | U/mL at day 3 | U/mg at day 3 |
| glucose control (2%)* | 0 | 0 | 0.28 ± 0.17 | NA |
| lactose (1.0 g/L) | 15 | 2.92 | 0.64 | 0.64 |
| cellobiose (1.0 g/L) | 15 | 2.92 | 0.34 | 0.34 |
| sophorose (0.13 g/L) | 2.0 | 0.38 | 3.58 | 26.9 |
| sophorose (1.3 g/L) | 20 | 3.90 | 15.0 | 11.2 |
| Natural (unmodified) sophorolipid mixture (1.1 g/L)** | 16 | ~1.57 | 2.90 | 2.72 |
| Acid-treated sophorolipid mixture (0.15 g/L)** | 2.2 | ~0.24 | 1.50 | 10.2 |
| Acid-treated sophorolipid mixture (1.1 g/L)** | 16 | ~1.77 | 14.9 ± 2.6 | 13.9 ± 2.4 |
| Fraction 1 of acid-treated sophorolipid (0.033 g/L)** | 0.5 | 0.050 | 24.7 | 741.0 |
| Fraction 2 of acid-treated sophorolipid (0.073 g/L)** | 1.1 | 0.12 | 18.8 | 256.4 |

*All media contain 2% glucose as the carbon source.
**Both the natural and acid-treated sophorolipid mixtures were treated to remove residual sophorose.

As seen in Table 7 above, the acid-treated sophorolipid mixture was observed to have greater induction power than known inducers, lactose and cellobiose, and the natural sophorolipid mixture. The specific induction power of the acid-treated sophorolipid mixture at 1.1 g/L (1.77 mM) was observed to be an order of magnitude higher than lactose and cellobiose at 1.0 g/L, and at least five times greater than the natural sophorolipid mixture at 1.1 g/L.

Fractions 1 and 2 isolated from the acid-treated sophorolipid mixture were also observed to be highly inductive, showing cellulase activity greater than the acid-treated sophorolipid mixture, the natural sophorolipid mixture and the known inducers (lactose, cellobiose and sophorose). For example, as seen in Table 7 above, the two fractions had specific induction powers that were several hundred times to a thousand times greater than that of lactose and cellobiose. Fraction 1 at 0.033 g/L (0.050 mM) had a specific induction power that was about thirty times greater than sophorose on a mass basis and about fifty times on a molar basis, and about two hundred to three hundred times greater than the natural sophorolipid mixture. Moreover, fraction 2 at 0.073 g/L (0.12 mM) was observed to have specific induction powers about ten times greater than sophorose on a mass basis and twenty times on a molar basis, and about one hundred times greater than the natural sophorolipid mixture.

Fractions 1 and 2 were also observed by LC-MS to contain a molar mass of 664 (665 [M+H]$^+$, 682 [M+NH$_4$]$^+$, FIG. 3E) and 622 (623 [M+H]$^+$, FIG. 3F), respectively. The 664 molar mass was determined to correspond to a monoacetylated sophorolipid ester, esterified at the C4" position with a fatty alcohol. The 622 molar mass was determined to correspond to a deacetylated sophorolipid ester, esterified at the C4" position with a fatty alcohol. The structure of the sophorolipid esters in these two fractions were further confirmed by analysis using nuclear magnetic resonance (NMR; Varian 500 mHz) and in-source fragmentation studies using mass spectroscopy (MS).

Based on the spectra of $^1$H NMR, $^{13}$C-NMR, and two-dimensional $^{13}$C-$^1$H HSQC NMR, fraction 1 was confirmed to be a 6" monoacetylated sophorolipid ester, esterified at C4" position with an 18-carbon monounsaturated fatty alcohol hydroxylated at the C17 position of the fatty alcohol chain. The assignments of protons and carbons observed from analysis of fraction 1 are summarized in Table 8 below.

TABLE 8

NMR peak assignment of $^{13}$C and $^1$H signals for fraction 1

| Functional groups | $^{13}$C-NMR δ(ppm) | $^1$H-NMR δ(ppm) |
|---|---|---|
| Sophorose | | |
| 1' | 92.4 | 5.31 |
| 1" | 104.7 | 4.53 |
| 2' | 82.1 | 3.42 |
| 2" | 74.1 | 3.40 |
| 3' | 74.1 | 3.56 |
| 3" | 72.3 | 3.85 |
| 4' | 70.2 | 3.36 |
| 4" | 70.6 | 4.82 |
| 5' | 71.9 | 3.66 |
| 5" | 67.3 | 3.68 |
| 6' a, b | 61.4 | 3.68, 3.78 |
| 6" a, b | 62.6 | 4.08, 4.14 |
| Acetyl group | | |
| —C═O | 171.2 | |
| CH3 | 19.5 | 2.04 |
| Acyl group | | |
| 1 | 172.3 | |
| 2 | 33.7 | 2.36 |
| 3 | 24.6 | 1.62 |
| 4-7, 12-15 | 25.6-29.6 | 1.27-1.46 |
| 8, 11 | 26.9 | 2.00-2.05 |
| 9, 10 | 129.6 | 5.34 |
| 16 | 39.0 | 1.40 |
| 17 | 71.5 | 3.78 |
| 18 | 22.2 | 1.14 |

The results from the $^1$H NMR spectrum of fraction 2 were similar to the results from the $^1$H NMR spectrum of fraction 1, except that a singlet peak at 2.04 ppm was not observed. This observation suggests the presence of a deacetylated sophorose ester, esterified at C4" position with an 18-carbon monounsaturated fatty alcohol hydroxylated at C17 position of the fatty alcohol chain.

Thus, this Example demonstrated that a monoacetylated sophorose ester (acetylated at the C6" position) and a deacetylated sophorose ester, both of which were esterified at C4" position with an 18-carbon monounsaturated fatty alcohol hydroxylated at C17 position of the fatty alcohol chain, were the active inducers in an acid-treated sophorolipid mixture, and contributed to significantly greater cellulase production in *Trichoderma*.

What is claimed is:

1. A compound having a structure of formula (II):

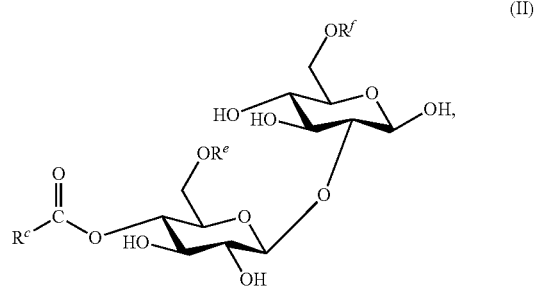

wherein:

R$^c$ is an aliphatic moiety;

R$^e$ is H or C(O)CH$_3$; and

R$^f$ is H or C(O)CH$_3$.

2. The compound of claim 1, wherein R$^c$ is an aliphatic moiety selected from the group consisting of unsubstituted C1-C24 alkyl, substituted C1-C24 alkyl, unsubstituted C2-C24 alkenyl, substituted C2-C24 alkenyl, unsubstituted C2-C24 alkynyl, and substituted C2-C24 alkynyl.

3. The compound of claim 1, wherein R$^c$ is an aliphatic moiety selected from the group consisting of unsubstituted C1-C24 alkyl, C1-C24 alkyl substituted with hydroxyl, unsubstituted C2-C24 alkenyl, C2-C24 alkenyl substituted with hydroxyl, unsubstituted C2-C24 alkynyl, and C2-C24 alkynyl substituted with hydroxyl.

4. The compound of claim 1, wherein the compound has a structure of formula (IIa), (IIb), (IIc) or (IId):

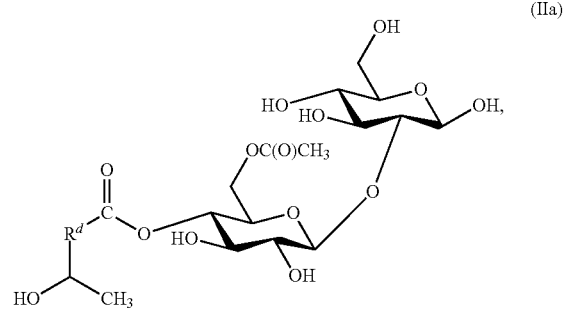

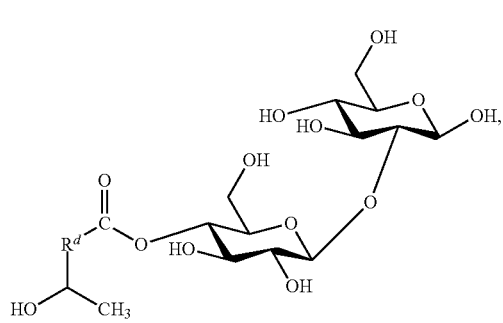
(IIb)
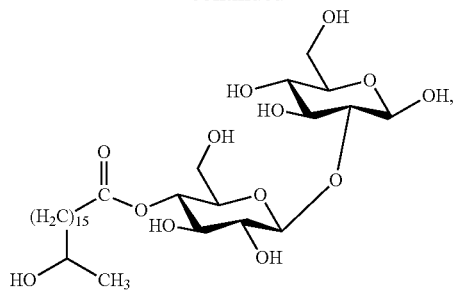
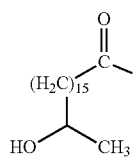
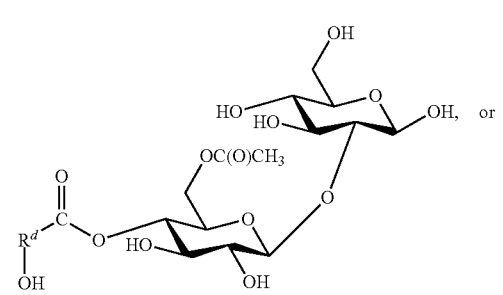
(IIc)
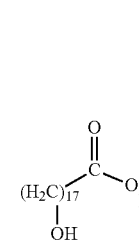
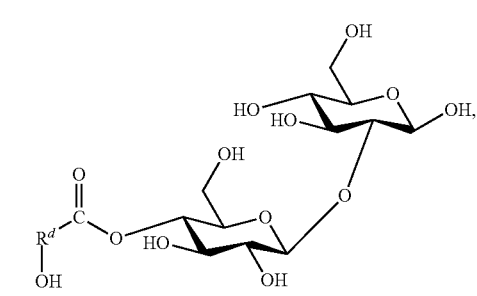
(IId)
wherein $R^d$ is an aliphatic moiety.
5. The compound of claim 4, wherein $R^d$ is an aliphatic moiety selected from the group consisting of unsubstituted C1-C24 alkylene, unsubstituted C2-C24 alkenylene, and unsubstituted C3-C24 alkynylene.
6. The compound of claim 1, wherein the compound is selected from the group consisting of:
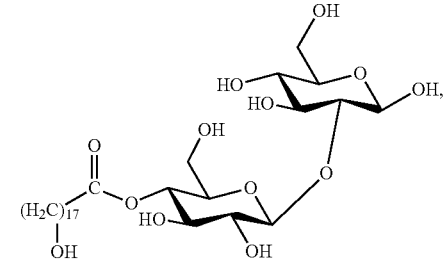
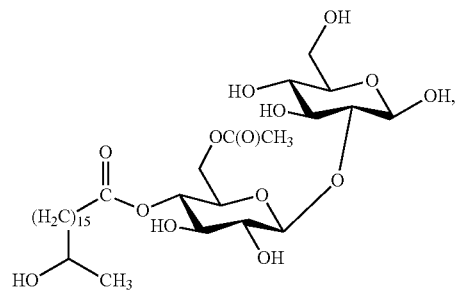
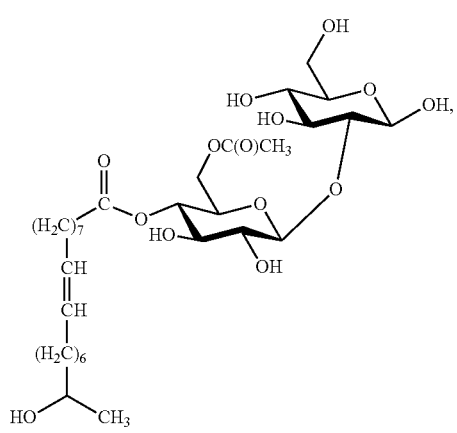

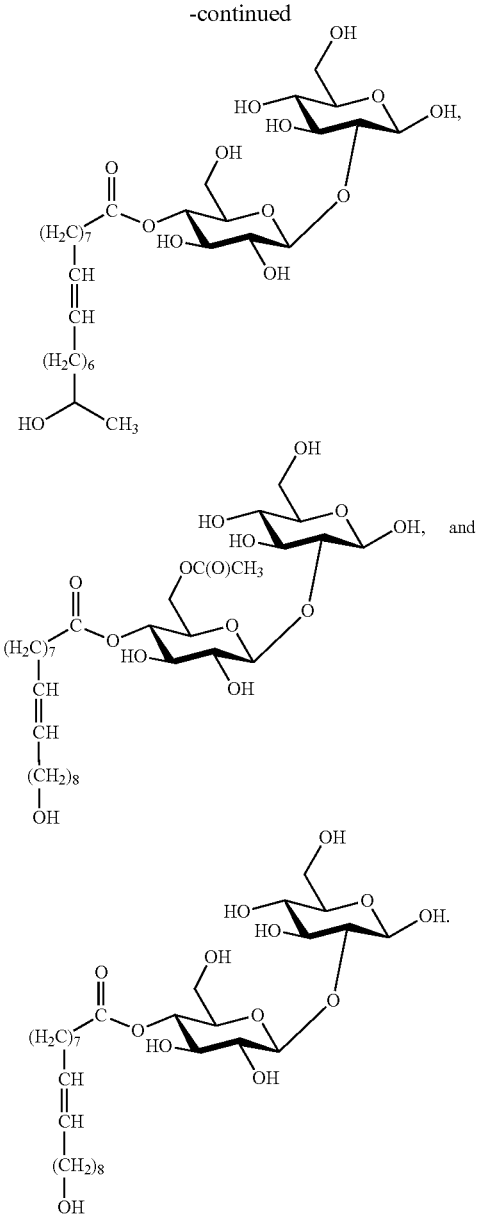

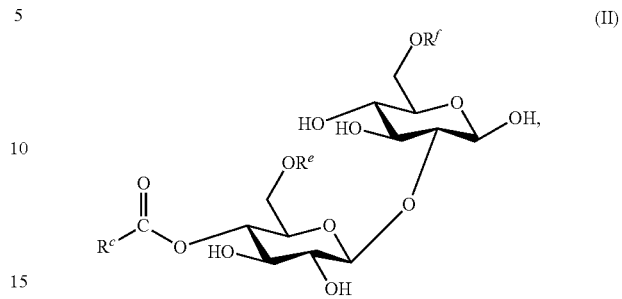

7. A composition comprising:
one or more compounds having a structure of formula (II):

wherein:
$R^c$ is an aliphatic moiety;
$R^e$ is H or C(O)CH3; and
$R^f$ is H or C(O)CH3; and
one or more compounds selected from the group consisting of a monoacetylated acidic sophorolipid, a diacetylated acidic sophorolipid, a deacetylated acidic sophorolipid, a monoacetylated lactonic sophorolipid, a diacetylated lactonic sophorolipid, a deacetylated lactonic sophorolipid, a monoacetylated glucolipid, a diacetylated glucolipid, and a deacetylated glucolipid.

8. The composition of claim 7, wherein the one or more compounds having the structure of formula (II) is at least 0.5% by weight of the composition.

9. A method for producing a composition of claim 7, comprising:
(a) providing a natural sophorolipid mixture by fermentation of a biomass using *Candida bombicola* in a fermentation media; and
(b) contacting the natural sophorolipid with an acid solution.

10. The method of claim 9, wherein the contacting of the natural sophorolipid mixture with the acid solution further comprises heating the natural sophorolipid mixture and the acid solution.

11. The method of claim 10, wherein the natural sophorolipid mixture and the acid solution are heated at a temperature of at least 50° C.

* * * * *